(12) United States Patent
Baer et al.

(10) Patent No.: US 9,926,654 B2
(45) Date of Patent: Mar. 27, 2018

(54) NONWOVEN FABRICS COMPRISED OF INDIVIDUALIZED BAST FIBERS

(71) Applicant: Georgia-Pacific Consumer Products LP, Atlanta, GA (US)

(72) Inventors: Samuel Charles Baer, Atlanta, GA (US); Micheal Shea Lerch, Roswell, GA (US); Alan Edward Wright, Roswell, GA (US)

(73) Assignee: GPCP IP Holdings LLC, Atlanta, GA (US)

( * ) Notice: Subject to any disclaimer, the term of this patent is extended or adjusted under 35 U.S.C. 154(b) by 367 days.

(21) Appl. No.: 13/835,194

(22) Filed: Mar. 15, 2013

(65) Prior Publication Data

US 2014/0066872 A1 Mar. 6, 2014

Related U.S. Application Data

(60) Provisional application No. 61/697,073, filed on Sep. 5, 2012, provisional application No. 61/776,247, filed on Mar. 11, 2013.

(51) Int. Cl.
*D04H 1/46* (2012.01)
*B32B 5/02* (2006.01)
(Continued)

(52) U.S. Cl.
CPC ............. *D04H 1/46* (2013.01); *A61F 13/538* (2013.01); *B01D 39/083* (2013.01); *B01D 39/1615* (2013.01); *B01D 39/1623* (2013.01); *B01D 39/18* (2013.01); *B32B 3/10* (2013.01); *B32B 5/022* (2013.01); *B32B 5/024* (2013.01); *B32B 5/26* (2013.01); *B32B 7/12* (2013.01); *B32B 27/12* (2013.01); *B32B 27/32* (2013.01); *B32B 27/40* (2013.01); *B32B 38/0012* (2013.01);
(Continued)

(58) Field of Classification Search
CPC ....... C08L 97/02; D04H 1/425; A61K 8/0208; D21H 27/002; D21H 27/02
USPC ............................................ 442/153; 8/116.1
See application file for complete search history.

(56) References Cited

U.S. PATENT DOCUMENTS

| | | | |
|---|---|---|---|
| 797,749 A | 8/1905 | Robinson et al. | |
| 2,045,095 A | 7/1934 | Osborne | |

(Continued)

FOREIGN PATENT DOCUMENTS

| | | |
|---|---|---|
| CA | 841938 A | 5/1970 |
| EP | 0408199 A1 | 6/1990 |

(Continued)

OTHER PUBLICATIONS

Bast Fibers LLC market link to Non-wovens (2007), available at http://bastfibersllc.com/markets/nonwovens.html.*

(Continued)

*Primary Examiner* — Jeremy R Pierce
(74) *Attorney, Agent, or Firm* — Ram W. Sabnis

(57) ABSTRACT

Nonwoven textile fabrics in accordance with the present invention are formed primarily of individualized bast fibers substantially free of pectin. The nonwoven fabric can include staple fibers to a lesser extent than the individualized bast fibers. Individualized bast fibers include fibers derived from the flax and hemp plants. The nonwoven textile fabric is formed into a web while in a dry state and subsequently bonded to produce a nonwoven fabric.

135 Claims, 2 Drawing Sheets

(51) Int. Cl.

| | | |
|---|---|---|
| *B32B 3/10* | (2006.01) | |
| *B32B 38/00* | (2006.01) | |
| *D04H 1/50* | (2012.01) | |
| *B32B 5/26* | (2006.01) | |
| *A61F 13/538* | (2006.01) | |
| *B01D 39/08* | (2006.01) | |
| *D01G 15/00* | (2006.01) | |
| *D04H 1/492* | (2012.01) | |
| *D04H 1/542* | (2012.01) | |
| *D04H 1/58* | (2012.01) | |
| *D04H 1/4266* | (2012.01) | |
| *B01D 39/16* | (2006.01) | |
| *B01D 39/18* | (2006.01) | |
| *B32B 7/12* | (2006.01) | |
| *B32B 27/12* | (2006.01) | |
| *B32B 27/32* | (2006.01) | |
| *B32B 27/40* | (2006.01) | |
| *D04H 1/64* | (2012.01) | |
| *B32B 37/06* | (2006.01) | |
| *B32B 37/12* | (2006.01) | |
| *B32B 37/22* | (2006.01) | |

(52) U.S. Cl.
CPC ........... *D01G 15/00* (2013.01); *D04H 1/4266* (2013.01); *D04H 1/492* (2013.01); *D04H 1/50* (2013.01); *D04H 1/542* (2013.01); *D04H 1/58* (2013.01); *D04H 1/64* (2013.01); *B01D 2239/064* (2013.01); *B01D 2239/1225* (2013.01); *B32B 37/06* (2013.01); *B32B 37/12* (2013.01); *B32B 37/223* (2013.01); *B32B 2262/02* (2013.01); *B32B 2262/06* (2013.01); *B32B 2262/067* (2013.01); *B32B 2262/14* (2013.01); *B32B 2305/188* (2013.01); *B32B 2305/20* (2013.01); *B32B 2307/724* (2013.01); *B32B 2555/02* (2013.01); *Y10T 428/2481* (2015.01); *Y10T 442/3065* (2015.04); *Y10T 442/608* (2015.04); *Y10T 442/627* (2015.04)

(56) References Cited

U.S. PATENT DOCUMENTS

| | | | |
|---|---|---|---|
| 2,407,227 A | | 11/1943 | Earle |
| 2,689,199 A | | 9/1954 | Pesce |
| 3,301,746 A | | 1/1967 | Sanford et al. |
| 3,485,706 A | | 12/1969 | Evans |
| 3,785,922 A | | 5/1970 | Keller |
| 3,554,862 A | | 1/1971 | Hervey et al. |
| 3,563,241 A | | 2/1971 | Evans |
| 3,849,241 A | | 11/1974 | Butin et al. |
| 3,917,785 A | | 11/1975 | Kalwaites |
| 4,014,635 A | | 3/1977 | Kroyer |
| 4,081,319 A | | 3/1978 | Conway |
| 4,100,324 A | | 7/1978 | Anderson et al. |
| 4,144,122 A | | 3/1979 | Emanuelsson et al. |
| 4,200,488 A | | 4/1980 | Brandon et al. |
| 4,442,161 A | | 4/1984 | Kirayoglu et al. |
| 4,469,734 A | | 9/1984 | Minto et al. |
| 4,476,323 A | | 10/1984 | Hellsten et al. |
| 4,559,157 A | | 12/1985 | Smith et al. |
| 4,617,383 A | * | 10/1986 | Jaskowski ............ C08B 37/0045 435/275 |
| 4,640,810 A | | 2/1987 | Laursen et al. |
| 4,667,890 A | | 5/1987 | Gietman, Jr. |
| 4,690,821 A | | 9/1987 | Smith et al. |
| 4,755,421 A | | 7/1988 | Manning et al. |
| 4,787,699 A | | 11/1988 | Moulin |
| 4,795,476 A | | 1/1989 | Bean et al. |
| 4,808,467 A | | 2/1989 | Suskind et al. |
| 4,818,464 A | | 4/1989 | Lau |
| 5,205,835 A | | 4/1993 | Tieckelmann et al. |
| 5,284,703 A | | 2/1994 | Everhart et al. |
| 5,292,581 A | | 3/1994 | Viazmensky et al. |
| 5,350,624 A | | 9/1994 | Georger et al. |
| 5,389,202 A | | 2/1995 | Everhart et al. |
| 5,573,637 A | | 11/1996 | Ampulski et al. |
| 5,674,591 A | | 10/1997 | James et al. |
| 5,683,794 A | | 11/1997 | Wadsworth et al. |
| 5,695,868 A | * | 12/1997 | McCormack ............ 442/389 |
| 5,843,057 A | * | 12/1998 | McCormack ............ A41D 31/02 442/393 |
| 5,853,538 A | | 12/1998 | Reiner |
| 5,891,126 A | | 4/1999 | Osborn, III et al. |
| 5,948,710 A | * | 9/1999 | Pomplun ............ D04H 1/565 442/340 |
| 5,958,186 A | | 9/1999 | Holm et al. |
| 5,985,186 A | | 11/1999 | Kasprzyk et al. |
| 6,037,407 A | | 3/2000 | Derian et al. |
| 6,051,749 A | | 4/2000 | Schulz |
| 6,163,943 A | | 12/2000 | Johansson et al. |
| 6,423,397 B1 | | 7/2002 | Roussel |
| 6,713,413 B2 | | 3/2004 | Kruegler |
| 6,762,138 B2 | | 7/2004 | Ferreira et al. |
| 6,884,837 B2 | | 4/2005 | Kohlhammer et al. |
| 6,994,865 B2 | | 2/2006 | Branham et al. |
| 7,432,219 B2 | | 10/2008 | Strandqvist et al. |
| 7,481,843 B2 | | 1/2009 | Xu |
| 7,732,357 B2 | | 6/2010 | Annis et al. |
| 7,892,397 B2 | | 2/2011 | Luo et al. |
| 8,133,825 B2 | | 3/2012 | Bunyard et al. |
| 8,287,986 B2 | | 10/2012 | Huss et al. |
| 8,293,072 B2 | | 10/2012 | Super et al. |
| 8,603,802 B2 | | 12/2013 | Sung et al. |
| 2001/0027545 A1 | | 10/2001 | Fujiwara |
| 2003/0065059 A1 | * | 4/2003 | Krishnaswamy ........ C08J 5/045 524/1 |
| 2003/0211802 A1 | | 11/2003 | Keck et al. |
| 2003/0215602 A1 | | 11/2003 | Andersson et al. |
| 2004/0048032 A1 | * | 3/2004 | Ankele ............ B29C 43/203 442/413 |
| 2005/0092417 A1 | | 5/2005 | Billgren et al. |
| 2005/0136773 A1 | | 6/2005 | Yahiaoui et al. |
| 2005/0136779 A1 | | 6/2005 | Stralin et al. |
| 2005/0245151 A1 | | 11/2005 | Annis et al. |
| 2005/0245161 A1 | | 11/2005 | Sain et al. |
| 2008/0153375 A1 | | 6/2008 | Wilfong et al. |
| 2008/0261476 A1 | | 10/2008 | Strandqvist et al. |
| 2009/0092835 A1 | * | 4/2009 | Xu ............ D01C 1/02 428/401 |
| 2009/0104430 A1 | | 4/2009 | Cordial et al. |
| 2010/0093245 A1 | * | 4/2010 | Bradley et al. ............ 442/341 |
| 2010/0130086 A1 | | 5/2010 | Dorsey et al. |
| 2010/0147472 A1 | * | 6/2010 | Sung ............ D01C 1/02 162/49 |
| 2010/0203291 A1 | | 8/2010 | Dyer et al. |
| 2010/0203306 A1 | | 8/2010 | Fingal et al. |
| 2010/0240113 A1 | * | 9/2010 | Liu ............ D01C 1/04 435/189 |
| 2011/0057346 A1 | * | 3/2011 | Nunn ............ D04H 1/4274 264/103 |
| 2011/0236665 A1 | | 9/2011 | Roque et al. |
| 2011/0250813 A1 | | 10/2011 | Bradley et al. |
| 2011/0312066 A1 | * | 12/2011 | Sung ............ D01C 1/02 435/277 |
| 2012/0021171 A1 | | 1/2012 | Riviere et al. |
| 2012/0046394 A1 | * | 2/2012 | Lu ............ C08K 7/02 524/9 |
| 2012/0144611 A1 | | 6/2012 | Baker et al. |
| 2012/0199301 A1 | | 8/2012 | Strandqvist |
| 2013/0198984 A1 | | 8/2013 | Strandqvist |
| 2013/0220151 A1 | | 8/2013 | Sauter et al. |

FOREIGN PATENT DOCUMENTS

| | | |
|---|---|---|
| EP | 331862 A1 | 7/1999 |
| EP | 0931862 A1 * | 7/1999 |
| EP | 1090176 A1 | 4/2001 |
| EP | 1350456 A1 | 10/2003 |
| JP | 2001322196 A | 11/2001 |

(56) References Cited

FOREIGN PATENT DOCUMENTS

| JP | 2008106383 A | 5/2008 |
|---|---|---|
| JP | 2008240177 A | 10/2008 |
| WO | 9710100 | 3/1997 |
| WO | 9826808 | 6/1998 |
| WO | 9937834 A1 | 7/1999 |
| WO | 03099886 A1 | 12/2003 |
| WO | 2005025865 A1 | 3/2005 |
| WO | 2007140054 A1 | 12/2007 |
| WO | 2007140578 A1 | 12/2007 |
| WO | 20090286059 A1 | 11/2009 |
| WO | 2011148136 A2 | 12/2011 |
| WO | 2012050494 A1 | 4/2012 |
| WO | 2015023558 A1 | 2/2015 |

OTHER PUBLICATIONS

Lee et al., "Antimicrobial and Blood Repellent Finishes for Cotton and Nonwoven Fabrics Based on Chitosan and Fluropolymers", Textile Research Journal, 69 (2), Feb. 1999; pp. 104-112.

Soap and Cosmetics "New Chemical Perspectives" Soap and Cosmetics, vol. 76, No. 3, www.soapandcosmetics.com; Mar. 2000, pp. 12-13, Best Available Copy.

Batra, Subhash Kumar, et al.; "Introduction to Nonwovens Technology"; DEStech Publications, Inc.; p. 131-160; 2012.

Floyd, Don E.; "Polyamide Resins"; Reinhold Publishing Corporation; p. 1-227; 1996.

International Search Report and Written Opinion dated Jul. 28, 2014 for Application No. PCT/US2014/021771.

International Search Report and Written Opinion dated Jun. 30, 2014 for Application No. PCT/US2014/021760.

International Search Report and Written Opinion dated Nov. 27, 2014 for Application No. PCT/US2014/050478.

International Search Report and Written Opinion dated Dec. 2, 2013 for Application No. PCT/US2013/057228.

International Search Report and Written Opinion dated Oct. 23, 2015 for Application No. PCT/US2015/044138.

Chinese Search Report dated Mar. 3, 2016 for Application No. 201380046325.7.

European Search Report dated Mar. 22, 2016 for Application No. 13835305.7-1308 / 2893068.

English translated Japanese Office Action dated Mar. 14, 2017.

\* cited by examiner

NONWOVEN FABRICS COMPRISED OF INDIVIDUALIZED BAST FIBERS

CROSS-REFERENCE TO RELATED APPLICATIONS

This application claims benefit of U.S. Provisional Patent Application Ser. No. 61/697,073, filed Sep. 5, 2012, and U.S. Provisional Patent Application Ser. No. 61/776,247, filed Mar. 11, 2013, both of which are incorporated herein in their entirety.

TECHNICAL FIELD OF THE INVENTION

The present invention relates generally to nonwoven textile fabrics. More specifically, the present invention relates to a nonwoven textile fabric comprised primarily of individualized bast fibers.

BACKGROUND OF THE INVENTION

Fibers utilized to produce woven and nonwoven textiles fall into the two broad categories: man-made and natural. Common man-made fibers include, for example, polyester, nylon, and polypropylene. Such thermoplastic polymers are melt spun into filaments which can be either air formed into nonwoven textiles directly as described in U.S. Pat. No. 2,689,199, which is incorporated herein in its entirety by reference, or cut into finite length fibers (known commonly as "staple fibers") which can be formed into threads and yarn for woven or knit textiles. In addition, staple fibers can be formed directly into randomly oriented fiber webs and subsequently bonded together by a variety of means to form a nonwoven textile fabric. Such staple fibers generally are kinked when employed in nonwoven webs.

The most widely known natural fibers are cotton, wool, and silk. Wool and silk are exclusively used for woven textiles. Cotton is the dominant fiber for woven textiles although it also has minor utilization in nonwoven textiles. Cotton has limited use for modern nonwoven textile production due to its tendency to form fiber bundles when processed with the high speed carding typical of nonwoven production lines.

Wood pulp is one of the most common natural fibers and primarily is used for papermaking. Yet, wood pulp has a significant presence in the nonwoven textile industry when combined with man-made filament or staple fiber and the hydroentangling web bonding process. See, for example, U.S. Pat. Nos. 4,442,161 and 5,284,703, both of which are incorporated herein in their entirety by reference. Wood pulp has no direct presence in the woven textile industry. Rather, cellulose, the natural polymer that constitutes wood pulp fibers and other vegetative matter, is formed into a man-made class of filaments known as, for example, rayon (sometimes referred to as viscose), TENCEL®, lyocell, and derivatives thereof. Such man-made cellulosic fibers are used in both woven and nonwoven textiles. Such polymeric fibers are formed by chemically dissolving cellulosic matter, and spinning filaments from the cellulosic solution. For use in dry formed webs, man-made cellulosic fibers are typically crimped and cut into staple fibers. Fiber crimping is not required for wet formed webs.

Another major category of natural fibers is bast fibers. Bast fibers are found in the stalks of the flax, hemp, jute, ramie, nettle, Spanish broom, and kenaf plants, to name only a few. Typically, native state bast fibers are 1 to 4 meters in length. These long native state fibers are comprised of bundles of individual fibers which are straight and have a length between 20-100 mm. The bundled individual fibers are glued together by a class of plant resins called pectins.

Bast fibers have been used for at least 8,000 years for both woven textiles and cordage. However, such textiles and cordage were formed only with the native state bast fiber bundles. An example of a woven textile produced with flax bast fiber bundles is linen. More recently, as provided in U.S. Pat. No. 7,481,843, partially separated bast fiber is produced to form yarns and threads for woven textiles. However, yarns and threads are not suited for nonwoven fabrics.

Nonwoven web forming methods for natural and man-made staple fibers include wet forming. Wet forming is similar to the papermaking process, except that the ratio of forming water weight to fiber weight is much higher than that of conventional papermaking with wood pulp. The wet forming process accommodates staple fibers which are typically 6 mm-10 mm long and wood pulp fibers which are typically 2-4 mm long. However, a dry formed nonwoven web comprising individualized bast fibers is not presently available in the market.

Accordingly, there is a need for a nonwoven fabric which employs natural fibers having a length greater than 4 mm long and is not limited to wet forming. It is to solving this problem the present invention is directed.

SUMMARY OF THE INVENTION

In accordance with the present invention, a nonwoven fabric comprising a majority of plant-based fibers is described herein. The nonwoven fabric can include man-made fibers, such as petroleum based and reconstituted cellulosic fibers, but to a lesser extent than the plant-based fibers. In one aspect, the nonwoven fabric comprises a majority of individualized fibers which are substantially straight, plant-based, and substantially pectin-free and have a mean length greater than 6 millimeters (mm). In another aspect, the nonwoven fabric comprises a majority of fibers which are non-cotton, plant-based, and substantially pectin-free and have a mean length greater than 10 mm. Yet, in another aspect, the nonwoven fabric comprises a majority of individualized fibers which are substantially straight, plant-based, and have a mean length greater than 10 mm.

A class of fibers which can be utilized in the present invention are individualized bast fibers. Bast fibers are extracted from, but not limited to, flax, hemp, jute, ramie, nettle, Spanish broom, kenaf plants. The aforementioned individualized bast fibers can be employed in any combination.

Individualized bast fibers utilized in this invention are typically straight and are substantially pectin free. Conventional "individualized" bast fibers, however, may be only subjected to mechanical individualization, not chemical individualization required to substantially remove pectin content. Enzymatic individualization is a nonlimiting example of chemical individualization. For example, individualized bast fibers have less than 10% by weight of the pectin content of the naturally occurring fibers from which the substantially pectin-free fibers are derived. In another aspect, individualized bast fibers have less than 15% by weight of the pectin content of the naturally occurring fibers from which the substantially pectin-free fibers are derived. Still, in another aspect, individualized bast fibers have less than 20% by weight of the pectin content of the naturally occurring fibers from which the substantially pectin-free fibers are derived. Still, in another aspect, individualized bast fibers have less than 0.1% by weight, less than 0.15% by weight, or less than 0.20% by weight, of the pectin content of the naturally occurring fibers from which the substantially pectin-free fibers are derived.

Typically, individualized bast fibers have a mean length in a range between about 6 and 40 mm depending on the characteristics of the particular bast fibers and the cut length of the plant stalks prior to chemical processing. In one aspect, the individualized bast fibers have a mean length of at least 7 mm, at least 8 mm, at least 9 mm, and at least 10 mm. In another aspect, the individualized bast fibers have a mean length greater than 12 mm.

The nonwoven fabric can also comprise staple fibers derived from one or more source. Staple fibers include, but are not limited to, cellulosic fibers and thermoplastic fibers. An example of a cellulosic staple fiber comprises rayon. Thermoplastic fibers include the conventional polymeric fibers utilized in the nonwoven industry. Such fibers are formed from polymers which include, but are not limited to, a polyester such as polyethylene terephthalate; a nylon; a polyamide; a polypropylene; polyolefin such as polypropylene or polyethylene; a blend of two or more of a polyester, a nylon, a polyamide, or a polyolefin; a bi-component composite of any two of a polyester, a nylon, a polyamide, or a polyolefin; and the like. When thermoplastic fibers are used, the nonwoven fabric can be thermally bonded to apply a pattern to at least one surface of the nonwoven fabric. An example of a bi-component composite fiber includes, but is not limited to, a fiber having a core of one polymer and a sheath comprising a polymer different from the core polymer which completely, substantially, or partially encloses the core.

The nonwoven fabric can be formed of a majority of fibers comprising individual bast fibers with less than 10% by weight of the pectin content of the naturally occurring bundled bast fiber from which the individual bast fibers are derived. In another aspect, the individual bast fibers comprise less than 20% by weight of the pectin content of the naturally occurring bundled bast fiber. The individual bast fibers are formed into an unbounded web in the dry state. Moreover, such bast fibers have a mean length greater than 12 mm. In one aspect, the web is formed by a method employing a mechanical card. In another aspect, the web is formed by a method employing a combination of a mechanical card and a forced air stream. The dry web can be bonded by hydroentangling. In addition, the hydroentangled web can be treated with an aqueous adhesive and exposed to heat to bond and dry the web. Also, the dry web can be bonded by mechanical needle punching and/or passing a heated air stream through the web. Alternatively, the dry web can be bonded by applying an aqueous adhesive to the unbounded web and exposing the web to heat.

In one aspect, a nonwoven fabric comprises about 85 weight percent (wt. %) bast fibers and about 15 wt. % regenerated cellulose fibers, based upon total fiber weight. In another aspect, a nonwoven fabric comprises between about 75 wt. % to about 90 wt. % bast fibers and about 25 wt. % to about 10 wt. % regenerated cellulose fibers, based upon total fiber weight. Yet, in another aspect, a nonwoven fabric comprises about 70 wt. % bast fibers and about 30 wt. % regenerated cellulose fibers, based upon total fiber weight.

A method of making a nonwoven fabric comprising a majority of individualized fibers which are substantially straight, plant-based, and substantially pectin-free and have a mean length greater than 6 mm comprises chemically treating naturally occurring fibers bundled with pectin to substantially remove pectin and form substantially individualized fibers. The substantially individualized fibers are carded to form a randomly arrayed fiber web and then bonded to form the nonwoven fabric.

A laminate is disclosed herein comprising a nonwoven fabric made in accordance with the present invention. Specifically, the laminate comprises a nonwoven fabric, a film, and an adhesive. The nonwoven fabric comprises a majority of individualized fibers which are substantially straight, plant-based, and substantially pectin-free and have a mean length greater than 6 millimeters (mm). In another aspect, the nonwoven fabric comprises a majority of fibers which are non-cotton, plant-based, and substantially pectin-free and have a mean length greater than 10 mm. Yet, in another aspect, the nonwoven fabric comprises a majority of individualized fibers which are substantially straight, plant-based, and have a mean length greater than 10 mm. A class of fibers which can be utilized in the present invention are individualized bast fibers. Further, an adhesive is disposed between the fabric and the film. The film comprises a polyethylene polymer, a polyethylene copolymer, a polypropylene polymer, a polypropylene copolymer, a polyurethane polymer, a polyurethane copolymer, a styrenebutadiene copolymer, or linear low density polyethylene.

In another aspect, a laminate comprises a first nonwoven fabric and another fabric bonded to the first nonwoven fabric. The first nonwoven fabric is the fabric of the present invention, and the another fabric is at least one of a second nonwoven fabric or a woven fabric. Optionally, the second nonwoven fabric is an additional nonwoven fabric of the present invention.

A method of making the aforementioned laminate comprises chemically treating naturally occurring fibers bundled with pectin to substantially remove the pectin and form substantially individualized fibers, carding the substantially individualized fibers to form a randomly arrayed fiber web, and bonding the randomly arrayed fiber web to form the nonwoven fabric. The nonwoven fabric comprises a majority of individualized fibers which are substantially straight, plant-based, and substantially pectin-free and have a mean length greater than 6 mm. Further, the nonwoven fabric has a support surface. An adhesive is disposed onto either the support surface of the nonwoven fabric or a surface of a film. The film is disposed onto the support surface of the nonwoven fabric such that the adhesive is disposed between the nonwoven fabric and the film, thereby bonding the film to the nonwoven fabric to form the laminate. Optionally, the nonwoven fabric, adhesive, and film are compressed to form the laminate. Heat can be applied during compression to aid in bonding the film to the nonwoven fabric to form the laminate.

It is to be understood that the phraseology and terminology employed herein are for the purpose of description and should not be regarded as limiting. As such, those skilled in the art will appreciate that the conception, upon which this disclosure is based, may readily be utilized as a basis for the designing of other structures, methods, and systems for carrying out the present invention. It is important, therefore, that the claims be regarded as including such equivalent constructions insofar as they do not depart from the spirit and scope of the present invention.

Other advantages and capabilities of the present invention will become apparent from the following description taken in conjunction with the accompanying drawings showing the elements and the various aspects of the present invention.

DETAILED DESCRIPTION OF INVENTION

Figure 1:
FIG. 1 is a photomicrograph of naturally occurring bast fibers from the flax plant.

A nonwoven fabric formed of a majority of individualized fibers which are substantially straight, plant-based, and substantially pectin-free and have a mean length greater than 6 mm is described. In another aspect, the nonwoven fabric comprises a majority of fibers which are non-cotton, plant-based, and substantially pectin-free and have a mean length greater than 10 mm. Yet, in another aspect, the nonwoven fabric comprises a majority of individualized fibers which are substantially straight, plant-based, and have a mean length greater than 10 mm.

As used herein, the term "plant-based fiber" means a fiber produced by and extracted from a plant as opposed to man-made fibers formed from cellulose. As used herein, the term "nonwoven" means a web or fabric having a structure of individual fibers or threads which are randomly interlaid, but not in an identifiable manner as in the case of a knitted or woven fabric. Examples of suitable nonwoven fabrics or webs include, but are not limited to, meltblown webs, spunbound webs, bonded carded webs, airlaid webs, coform webs, hydraulically entangled webs, and so forth.

A class of fibers which are utilized in the present invention are individualized bast fibers. Bast fibers are extracted from, but not limited to, flax, hemp, jute, ramie, nettle, Spanish broom, kenaf plants. The aforementioned individualized bast fibers can be employed in any combination.

Individualized bast fibers are typically straight and are substantially pectin free. For example, individualized bast fibers have less than 10% by weight of the pectin content of the naturally occurring fibers from which the substantially pectin-free fibers are derived. In another aspect, individualized bast fibers have less than 15% by weight of the pectin content of the naturally occurring fibers from which the substantially pectin-free fibers are derived. Still, in another aspect, individualized bast fibers have less than 20% by weight of the pectin content of the naturally occurring fibers from which the substantially pectin-free fibers are derived.

Typically, individualized bast fibers have a mean length in a range between about 6 and 40 mm depending on the characteristics of the particular bast fibers and the cut length of the plant stalks prior to chemical processing. In one aspect, the individualized bast fibers have a mean length of at least 7 mm, at least 8 mm, at least 9 mm, and at least 10 mm. In another aspect, the individualized bast fibers have a mean length greater than 12 mm.

The nonwoven fabric can also comprise staple fibers derived from one or more source. Staple fibers include, but are not limited to, cellulosic fibers and thermoplastic fibers. An example of a cellulosic staple fiber comprises rayon. Thermoplastic fibers include the conventional polymeric fibers utilized in the nonwoven industry. Such fibers are formed from polymers which include, but are not limited to, a polyester such as polyethylene terephthalate; a nylon; a polyamide; a polyolefin such as polypropylene or polyethylene; a blend of two or more of a polyester, a nylon, a polyamide, or a polyolefin; a bi-component composite of any two of a polyester, a nylon, a polyamide, or a polyolefin; and the like. An example of a bi-component composite fiber includes, but is not limited to, a fiber having a core of one polymer and a sheath comprising a polymer different from the core polymer which completely, substantially, or partially encloses the core.

The nonwoven fabric can be formed of a majority of fibers comprising individual bast fibers with less than 10% by weight of the pectin content of the naturally occurring bundled bast fiber from which the individual bast fibers are derived. In another aspect, the individual bast fibers comprise less than 20% by weight of the pectin content of the naturally occurring bundled bast fiber. The individual bast fibers are formed into an unbounded web in the dry state. Moreover, such bast fibers have a mean length greater than 12 mm. In one aspect, the web is formed by a method employing a mechanical card. In another aspect, the web is formed by a method employing a combination of a mechanical card and a forced air stream. The dry web can be bonded by hydroentangling, which is described in U.S. Pat. Nos. 3,485,706 and 5,958,186, both of which are incorporated herein in their entirety by reference. In addition, the hydroentangled web can be treated with an aqueous adhesive and exposed to heat to bond and dry the web. Also, the dry web can be bonded by mechanical needle punching and/or passing a heated air stream through the web. Alternatively, the dry web can be bonded by applying an aqueous adhesive to the unbounded web and exposing the web to heat.

As stated above, in one aspect, nonwoven fabrics in accordance with the present invention comprise a majority fiber content that is individualized bast fibers. Naturally occurring bundled bast fibers are chemically treated to remove the pectin holding the bundles together and separate the naturally occurring fibers into individual bast fibers. Pectin acts as natural glue which holds the individual bast fibers in the bundle. By removing the pectin and separating the individual bast fibers, the individualized bast fibers can be formed into a web while in a dry state prior to subsequent bonding by suitable means to form a nonwoven textile fabric.

Figure 2:
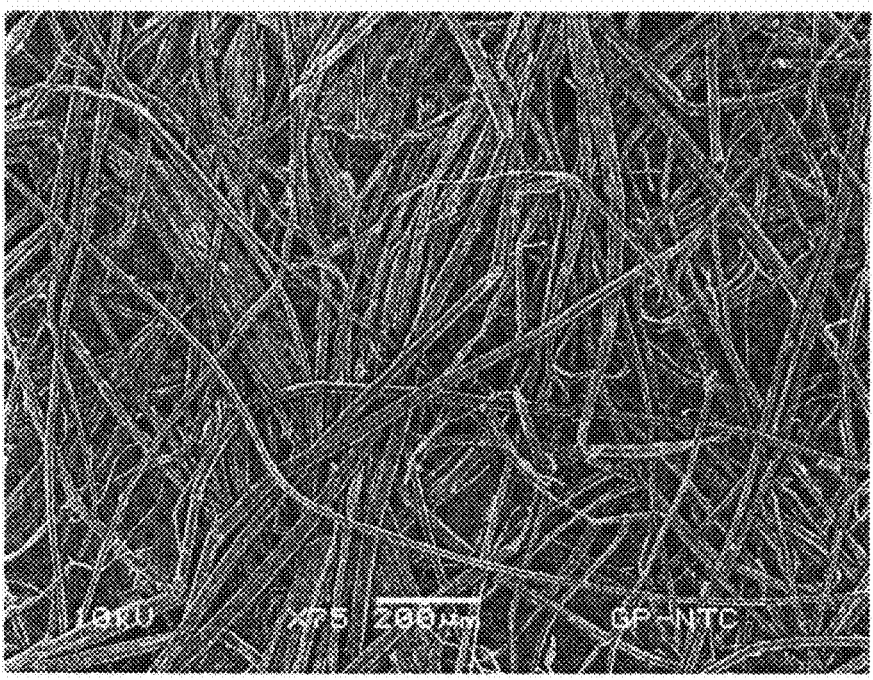
FIG. 2 is a photomicrograph of the individualized bast fibers substantially free of pectin.

FIG. 1 is a photomicrograph of naturally occurring bast fibers from the flax plant. The stack of small individual flax bast fibers that make up the bast fiber bundle are visible. FIG. 2 is a photomicrograph of the individual bast fibers after pectin removal from the flax bast fiber bundles shown in FIG. 1. As shown in FIG. 2, individual bast fibers are smooth and elongated. In addition, individual bast fibers do not have kinks or crimps. Use of such fibers to produce a dry-formed nonwoven fabric is novel. Moreover, because of the length of the individual bast fibers, they must be cut to a length of 2-6 mm to produce a wet-formed nonwoven fabric.

A nonwoven web of staple fibers can be formed by a mechanical process known as carding as described in U.S. Pat. No. 797,749, which is incorporated herein in its entirety by reference. The carding process can include an airstream component to randomize the orientation of the staple fibers when they are collected on the forming wire. Typically, the synthetic staple fiber length for a mechanically carded process is in the range of 38-60 mm. Longer lengths are possible depending on the set up of the card. A state of the art mechanical card, such as the Triitzschler-Fliessner EWK-413 card, can run staple fibers having significantly shorter length than the 38 mm noted above. Older card designs may require longer fiber length to achieve good formation and stable operation.

Another common dry web forming process is air-laid or air-forming. This process employs only air flow, gravity, and centripetal force to deposit a stream of fibers onto a moving forming wire that conveys the fiber web to a web bonding process. Air-laid processes are described in U.S. Pat. Nos. 4,014,635 and 4,640,810, both of which are incorporated herein in their entirety by reference. Pulp-based air-formed nonwoven webs frequently incorporate 10 to 20% of 4 to 6 mm long thermoplastic fibers that melt and bond the air-laid web together when the air-formed web is passed through ovens. It is possible to air-form a layer of 100% thermoplastic fiber in conjunction with a pulp-based layer, however, the fiber throughput rate declines significantly with increasing fiber length. Typically, such fiber lengths above 12 mm are commercially impractical.

Figure 3:
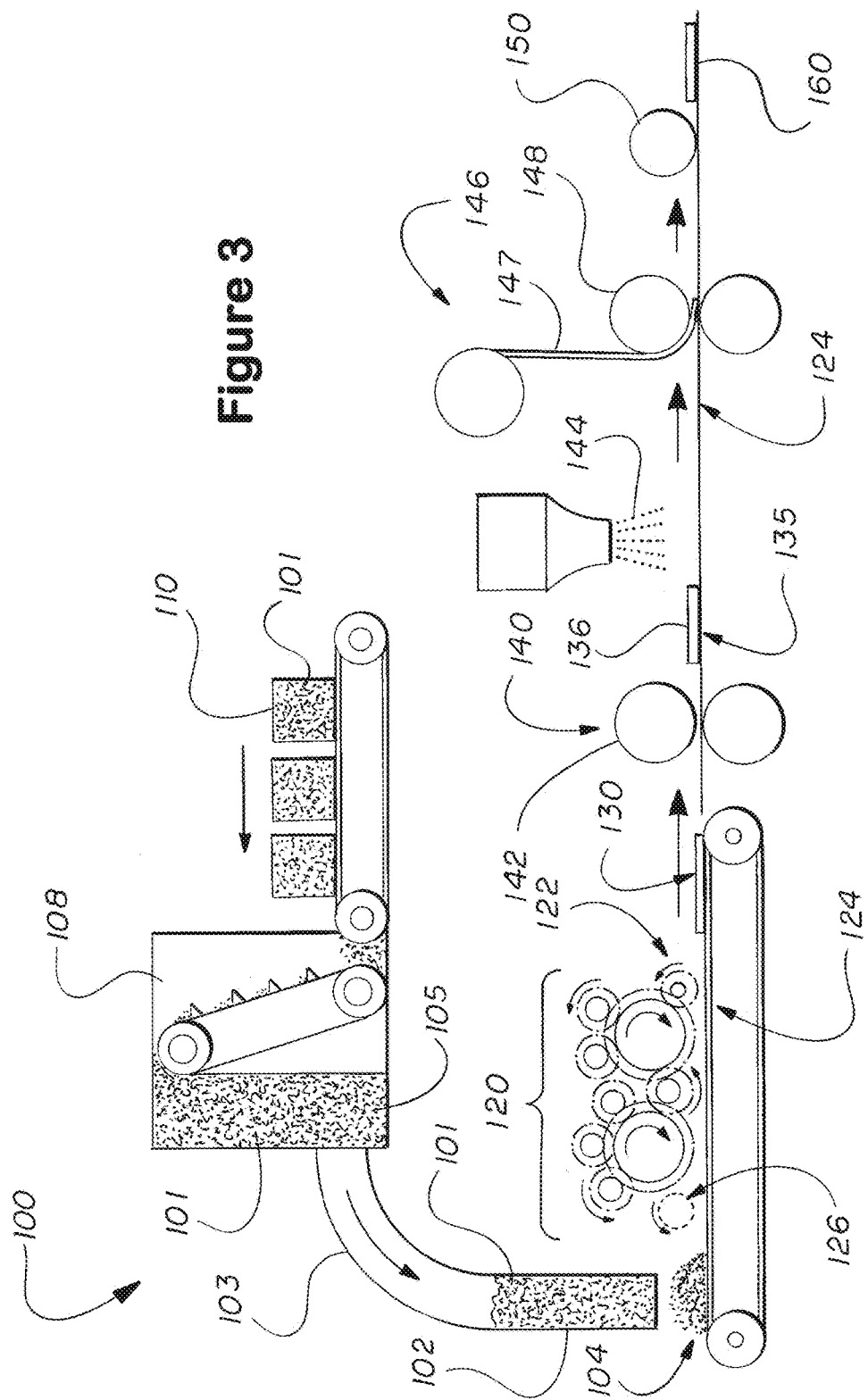
FIG. 3 is a process diagram of a carding process to form a nonwoven fabric in accordance with the present invention and a laminate employing such nonwoven fabric.

Referring to FIG. 3, in accordance with the present invention, it is possible to use a mechanical means such as a mechanical carding 100 process used for staple fibers to form full length, dry individualized bast fibers 101 into a randomly arrayed fiber web 130 that can then be transferred to a web bonding process to create a bast fiber based nonwoven fabric 135. This aspect is unique in that individual bast fibers, particularly those from the flax or hemp plants, do not have physical dimensions that are characteristic of a cardable staple fiber.

Naturally occurring bundled bast fibers first are chemically treated to substantially remove pectin and form substantially pectin free, individualized fibers 101. Dry, individualized fibers 101 can be incorporated into fiber bales 110. The fiber bales 110 are separated in a bale opener 108 and moved into a fiber accumulator 105. The accumulated fibers 101 can be air-conveyed 103 through a feed chute 102 and then deposited as a fiber feed mat 104 onto a forming wire 124. The air-conveyed process 103 randomizes the orientation of the fibers 101 when they are collected on the forming wire 124. The fiber feed mat 104 is fed through a fiber feed roll 126 into the fiber carding equipment 120, which further separates the fibers 101 into individualized, carded fibers. The fiber doffing roll 122 transfers the carded fibers back onto the forming wire 124 to form the fiber web 130. The fiber web 130 can then be transferred to web bonding equipment, such as thermal bonding equipment 140, which is discussed below, to form the nonwoven fabric 135. Optionally, the dry web can be bonded by hydroentangling. In addition, the hydroentangled web can be treated with an aqueous adhesive and exposed to heat to bond and dry the web. Also, the dry web can be bonded by mechanical needle punching and/or passing a heated air stream through the web. Alternatively, the dry web can be bonded by applying an aqueous adhesive to the unbounded web and exposing the web to heat.

A typical cardable staple fiber is 38 to 60 mm in length and has 5-10 crimps per inch of fiber length. The crimp in each fiber provides fiber to fiber cohesion. The combination of length and crimp gives the unbounded fiber web sufficient strength to allow web transfer between successive rollers in the carding equipment 120 and to be transferred from the card, to the collection wire 124, and then to bonding equipment 140, without a break in the web 130. In contrast, individualized bast fibers may have a length of only 20-25 mm or less and, more significantly, are straight fibers with no natural or mechanically induced crimps to facilitate fiber to fiber cohesion. For example, cotton fiber has a natural twist which generates high fiber to fiber cohesion. Individualized bast fibers are void of a natural twist. The artificial crimp applied to man-made fiber is an effort to mimic the fiber-to-fiber cohesion effect of the natural twist of cotton fiber. The fiber length and low fiber cohesion of individual bast fibers, according to conventional wisdom, renders them poor candidates for a dry web forming process such as carding. In addition, the natural fiber length of 20-25 mm is, however, too long to be processed at 100% concentration by web forming processes that are driven entirely by air or water air stream as described respectively in U.S. Pat. Nos. 4,014,635; 4,640,810; and 5,958,186. Nonetheless, in accordance with the present invention, a dry web forming process utilizing carding has been successfully employed to produce a nonwoven fabric comprising a majority of individualized bast fibers.

Thermal bonding 140 is also referred to as calendar bonding, point bonding, or pattern bonding, and is used to bond a fiber web 130 to form a nonwoven fabric 135. Thermal bonding 140 can also incorporate a pattern into the fabric. Thermal bonding 140 is described in PCT International Publication No. WO/2005/025865, which is incorporated herein by reference in its entirety. Thermal bonding 140 requires incorporation of thermoplastic fibers into the fiber web 130. Examples of thermoplastic fibers are discussed above. In thermal bonding 140, the fiber web 140 is bonded under pressure by passing through heated calendar rolls 42, which can be embossed with a pattern that transfers to the surface of the fiber web 130. During thermal bonding 140, the calendar rolls 142 are heated to a temperature at least between the glass transition temperature ($T_g$) and the melting temperature ($T_m$) of the thermoplastic material.

The nonwoven fabric of the present invention can be incorporated into a laminate 160 comprising the nonwoven fabric 135 and a film 146. Laminates 160 can be used in a wide variety of applications, such outer-covers for personal care products and absorbent articles, for example diapers, training paints, incontinence garments, feminine hygiene products, wound dressings, bandages, and the like.

To form a laminate, an adhesive 144 is applied to a support surface 136 of the nonwoven fabric 135 or a surface 147 of the film 146 (not shown). Examples of suitable adhesives include sprayable latex, polyalphaolefin, (commercially available as Rextac 2730 and Rextac 2723 from Huntsman Polymers, Houston, Tex.), and ethylene vinyl acetate. Additional commercially available adhesives include, but are not limited to, those available from Bostik Findley, Inc., Wauwatosa, Wis. Then, a film 146 is fed onto the forming wire 124 on top of the nonwoven fabric 135. Before application to the nonwoven fabric, the film 146 is stretched as desired. The nonwoven fabric 135 and film 146 are combined and compressed in a nip 148 to form the laminate 160. Although not required for pressure sensitive adhesives, the nip 148 can be maintained at a desired adhesive bonding temperature suitable for the adhesive employed, e.g. heat activated adhesions. The laminate can be cut 150, directed to a winder (not shown), or directed to further processing (not shown).

In addition to applying a film 144 to the nonwoven fabric 135, another fabric can be bonded to the nonwoven fabric 135 (not shown), which can be, for example another nonwoven fabric or a woven fabric (not shown). The nonwoven fabric can be a nonwoven fabric made in accordance with the present invention. An adhesive can be applied to either the nonwoven fabric 135 or the another fabric before nipping to form the laminate 160.

The films used in laminates can include, but are not limited to, polyethylene polymers, polyethylene copolymers, polypropylene polymers, polypropylene copolymers, polyurethane polymers, polyurethane copolymers, styrenebutadiene copolymers, or linear low density polyethylene. Optionally, a breathable film, e.g. a film comprising calcium carbonate, can be employed to form the laminate. Generally, a film is "breathable" if it has a water vapor transmission rate of at least 100 grams/square meter/24 hours, which can be measured, for example, by the test method described in U.S. Pat. No. 5,695,868, which is incorporated herein in its entirety by reference. Breathable films, however, are not limited to films comprising calcium carbonate. Breathable films can include any filler. As used herein, "filler" is meant to include particulates and other forms of materials which will not chemically interfere with or adversely affect the film, but will be substantially uniformly dispersed throughout the film. Generally, fillers are in particulate form and spherical in shape, with average diameters in the range between about 0.1 micrometers to about 7 micrometers. Fillers include, but are not limited to, organic and inorganic fillers.

The fibers of the present invention can be individualized by chemically treating the naturally occurring fibers to substantially remove pectin. Enzymatic treatment is a non-limiting example of a chemical treatment that can be used to substantially remove pectin. PCT International Publication No. WO 2007/140578, which is incorporated herein in its entirety by reference, describes a pectin removal technology which produces individualized hemp and flax fiber for application in the woven textile industry. Although individualized bast fiber is straight, it has fineness similar to cotton and has a length of at least 20 mm. As discussed above, individualized bast fibers can be spun into threads and yards as a precursor to woven textile production. The process to remove pectin described in WO 2007/140578 can be employed with the present invention.

The naturally occurring bundled bast fibers and the individualized bast fibers utilized in the present invention, in addition to visual and tactile inspection, can be distinguished by quantified measuring of the relative amounts of pectin present in the bundled versus the individualized bast fibers. A chemical test has been developed to make this relative quantification, which is based on the method described in WO 2007/140578. The test procedure is as follows:

Approximately 30 mg of fiber is exposed to 20 µL of Novozyme Pectinase from *Aspergillus niger* (50× dilution) in 800 µL of a 100 mM sodium citrate buffer that is adjusted to pH 4.5 with hydrochloric acid. The solution is heated to 40° C. for 1 hour. After heating, 50 µL of the liquid solution is removed and added to 1 mL of 10 mM sodium hydroxide. A 3.0 mL aliquot of a 0.5% solution of 4-hydroxy-benzhydrazide (prepared as a 5% solution in 0.5 M hydrochloric acid and diluted with 0.5 M sodium hydroxide to give a 0.5% solution) is added to the solution which is then heated in boiling water for 5 minutes. After cooling, the absorbance of the mixture is measured at 410 nm.

Standards of galacturonic acid are prepared in water, and 50 µL of these solutions are added to 1 mL aliquots of 10 mM sodium hydroxide. Colorimetric analysis of the reducing sugar is followed in the same manner as above.

Table 1 reports the results of a test in terms of the percentage of reduced sugar extracted from the fibers into an aqueous solution. The reduced sugar is pectin in its extracted form. Therefore, the relative fraction of reduced sugar in the aqueous solution correlates with the relative fraction of pectin attached to the bast fibers prior to the extraction test. As indicated in Table 1, individualized bast fibers after enzyme processing have less than 0.1% reduced sugar.

TABLE 1

Relative reduced sugar/pectin content of bast fibers before and after enzymatic treatment.

| | Reduced Sugar Percentage (%)* |
|---|---|
| Flax bast fiber bundles before enzyme processing | 1.1 |
| Individualized flax bast fibers after enzyme processing | Less Than 0.1 |

*Reduced sugar extraction is a proportional indicator for pectin content

A nonwoven fabric in accordance with the present invention was formed by carding individualized hemp fibers into a web. The web was lightly bonded with a needle loom in-line with the mechanical card employed to form the web. The lightly bonded web was collected on a roll, and the roll was subsequently unwound into a set of hydrojets. If needed, cohesion can be improved by blending into the web a 20% crimped polyester (polyethylene terephthalate (PET) staple fiber. When employing less modern equipment, the crimped staple fiber allows for continuous transfer of the unbounded web from the card to the forming wire. The properties of such hydroentangled hemp/PET material are shown in Table 2.

Additional nonwoven fabrics in accordance with the present invention have been produced on a state of the art carding and hydroentangling pilot line. The EWK-413 design card on this pilot line was able to process 100% individualized hemp and individualized flax bast fibers. Doffing of the web from the carding equipment to the forming wire was facilitated by a vacuum transfer roll. The physical properties of the nonwoven fabrics produced on this pilot line are compared to the properties of competitive materials in Table 3.

In addition, the pilot trials investigated hemp bast fibers that had only been partially individualized by the pectin removal process described in PCT International Publication No. WO 2007/140578. The results presented in Table 4 show an inverse correlation between the pectin content of the bast fibers and the strength of the resulting nonwoven fabric. Thus, pectin content in a collection of bast fibers can be employed as a predictor of the performance of a nonwoven web comprised of those fibers.

The nonwoven fabric of the present invention can be incorporated into a variety of products. Non-limiting examples of products include wipers (or wipes), such as wet wipers, dry wipers, or impregnated wipers, which include personal care wipers, household cleaning wipers, and dusting wipers. Personal care wipers can be impregnated with, e.g., emollients, humectants, fragrances, and the like. Household cleaning wipers or hard surface cleaning wipers can be impregnated with, e.g., surfactants (for example, quaternary amines), peroxides, chlorine, solvents, chelating agents, antimicrobials, fragrances, and the like. Dusting wipers can be impregnated with, e.g., oils.

Non-limiting examples of wipers include baby wipes, cosmetic wipes, perinea wipes, disposable washcloths, household cleaning wipes, such as kitchen wipes, bath wipes, or hard surface wipes, disinfecting and germ removal wipes, specialty cleaning wipes, such as glass wipes, mirror wipes, leather wipes, electronics wipes, lens wipes, and polishing wipes, medical cleaning wipes, disinfecting wipes, and the like. Additional examples of products include sorbents, medical supplies, such as surgical drapes, gowns, and wound care products, personal protective products for industrial applications, such as protective coveralls, sleeve protectors, and the like, protective coverings for automotive applications, and protective coverings for marine applications. The nonwoven fabric can be incorporated into absorbent cores, liners, outer-covers, or other components of personal care articles, such as diapers (baby or adult), training pants, feminine care articles (pads and tampons) and nursing pads. Further, the nonwoven fabric can be incorporated into fluid filtration products, such air filters, water filters, and oil filters, home furnishings, such as furniture backing, thermal and acoustic insulation products, agricultural application products, landscaping application products, and geotextile application products.

In one aspect, a nonwoven fabric comprises about 85 weight percent (wt. %) bast fibers and about 15 wt. % regenerated cellulose fibers, based upon total fiber weight. In another aspect, a nonwoven fabric comprises between about 75 wt. % to about 90 wt. % bast fibers and about 25 wt. % to about 10 wt. % regenerated cellulose fibers, based upon total fiber weight. Yet, in another aspect, a nonwoven fabric comprises about 70 wt. % bast fibers and about 30 wt. % regenerated cellulose fibers, based upon total fiber weight.

Examples of regenerated cellulose include, but are not limited to, rayon, lyocell, (e.g., TENCEL®), Viscose®, or any combination thereof. TENCEL® and Viscose® are commercially available from Lenzing Aktiengesellschaft, Lenzing, Austria.

As mentioned above, the nonwoven fabric can be a wet wipe. The wet wipe can be pre-moistened with a wetting composition, which can include at least one additive. The wetting composition can be any solution, including, but not limited to, an aqueous solution comprising at least one additive. Non-limiting examples of suitable additives are provided below. The wetting composition can be disposed on or impregnated within the nonwoven fabric by any method. Examples of such methods include, but are not limited to, soaking the nonwoven fabric in the wetting composition and spraying the wetting composition onto the nonwoven fabric.

As indicated above, a variety of additives can be employed with the non-woven fabric products described herein. Suitable additives include, but are not limited to: skin-care additives; odor control agents; detackifying agents if a binder is present in the non-woven fabric to reduce the tackiness of the binder; particulates; antimicrobial agents; preservatives; wetting agents and cleaning agents such as detergents, surfactants, and some silicones; emollients; surface feel modifiers for improved tactile sensation (e.g., lubricity) on the skin; fragrance; fragrance solubilizers; opacifiers; fluorescent whitening agents; UV absorbers; pharmaceuticals; and pH control agents, such as malic acid or potassium hydroxide.

Skin-care additives provide one or more benefits to the user, such as a reduction in the probability of having diaper rash and/or other skin damage caused by fecal enzymes. These enzymes, particularly trypsin, chymotrypsin and elastase, are proteolytic enzymes produced in the gastrointestinal tract to digest food. In infants, for example, the feces tend to be watery and contain, among other materials, bacteria, and some amounts of undegraded digestive enzymes. These enzymes, if they remain in contact with the skin for any appreciable period of time, may cause an irritation that is uncomfortable in itself and can predispose the skin to infection by microorganisms. As a countermeasure, skin-care additives include, but are not limited to, the enzyme inhibitors and sequestrants. The wetting composition can contain less than about 5 weight percent of skin-care additives based on the total weight of the wetting composition. More specifically, the wetting composition can contain from about 0.01 weight percent to about 2 weight percent of skin-care additives. Even more specifically, the wetting composition can contain from about 0.01 weight percent to about 0.05 weight percent of skin-care additives.

A variety of skin-care additives can be added to the wetting composition and the pre-moistened wipes of the present invention or included therein. For example, skin-care additives in the form of particles can be added to serve as fecal enzyme inhibitors, offering potential benefits in the reduction of diaper rash and skin damage caused by fecal enzymes. U.S. Pat. No. 6,051,749, which is incorporated herein by reference in its entirety, discloses organophilic clays in a woven or nonwoven web described as being useful for inhibiting fecal enzymes. Such materials can be used in the present invention, including reaction products of a long chain organic quaternary ammonium compound with one or more of the following clays: montmorillonite, bentonite, beidellite, hectorite, saponite, and stevensite. Other known enzyme inhibitors and sequestrants can be used as skin-care additives in the wetting composition of the present invention, including those that inhibit trypsin and other digestive or fecal enzymes, and inhibitors for urease. For example, enzyme inhibitors and anti-microbial agents may be used to prevent the formation of odors in body fluids. For example, urease inhibitors, which are also said to play a role in odor absorption, are disclosed by T. Trinh in PCT International Publication No. 98/26808, which is incorporated herein by reference in its entirety. Such inhibitors can be incorporated into the wetting composition and the pre-moistened wipes of the present invention and include transition metal ions and their soluble salts, such as silver, copper, zinc, ferric, and aluminum salts. The anion may also provide urease inhibition, such as borate, phytate, etc. Compounds of potential value include, but are not limited to, silver chlorate, silver nitrate, mercury acetate, mercury chloride, mercury nitrate, copper metaborate, copper bromate, copper bromide, copper chloride, copper dichromate, copper nitrate, copper salicylate, copper sulfate, zinc acetate, zinc borate, zinc phytate, zinc bromate, zinc bromide, zinc chlorate, zinc chloride, zinc sulfate, cadmium acetate, cadmium borate, cadmium bromide, cadmium chlorate, cadmium chloride, cadmium formate, cadmium iodate, cadmium iodide, cadmium permanganate, cadmium nitrate, cadmium sulfate, and gold chloride. Other salts known to have urease inhibition properties include ferric and aluminum salts, such as the nitrates, and bismuth salts. Other urease inhibitors include hydroxamic acid and its derivatives; thiourea; hydroxylamine; salts of phytic acid; extracts of plants of various species, including various tannins, e.g. carob tannin, and their derivatives such as chlorogenic acid derivatives; naturally occurring acids such as ascorbic acid, citric acid, and their salts; phenyl phosphoro diamidate/diamino phosphoric acid phenyl ester; metal aryl phosphoramidate complexes, including substituted phosphorodiamidate compounds; phosporamidates without substitution on the nitrogen; boric acid and/or its salts, including especially, borax, and/or organic boron acid compounds; the compounds disclosed in European Patent Application 408,199; sodium, copper, manganese, and/or zinc dithiocarbamate; quinones; phenols; thiurams; substituted rhodanine acetic acids; alkylated benzoquinones; formamidine disulphide; 1:3-diketones maleic anhydride; succinamide; phthalic anhydride; pehenic acid; N,N-dihalo-2-imidazolidinones; N-halo-2-oxazolidinones; thio- and/or acyl-phosphoryltnamide and/or substituted derivatives thereof, thiopyridine-N-oxides, thiopyridines, and thiopyrimidines; oxidized sulfur derivatives of diaminophosphinyl compounds; cyclotriphosphazatriene derivatives; bromo-nitro compounds; S-aryl and/or alkyl diamidophosphorothiolates; diaminophosphinyl derivatives; mono- and/or polyphosphorodiamide; alkoxy-1,2-benzothaizin compounds; ortho-diaminophosphinyl derivatives of oximes; 5-substituted-benzoxathiol-2-ones; N(diammophosphinyl)arylcarboxamides; etc.

Many other skin-care additives may be incorporated into the wetting composition and pre-moistened wipes of the present invention, including, but not limited to, sun blocking agents and UV absorbers, acne treatments, pharmaceuticals, baking soda (including encapsulated forms thereof), vitamins and their derivatives such as Vitamins A or E, botanicals such as witch hazel extract and aloe vera, allantoin, emollients, disinfectants, hydroxy acids for wrinkle control or anti-aging effects, sunscreens, tanning promoters, skin lighteners, deodorants and anti-perspirants, ceramides for skin benefits and other uses, astringents, moisturizers, nail polish removers, insect repellants, antioxidants, antiseptics, anti-inflammatory agents and the like. Useful materials for skin care and other benefits are listed in McCutcheon's 1999, Vol. 2: Functional Materials, MC Publishing Company, Glen Rock, N.J. Many useful botanicals for skin care are provided by Active Organics, Lewisville, Tex.

Suitable odor control additives for use in the wetting composition and pre-moistened wipes of the present invention include, but are not limited to, zinc salts; talc powder; encapsulated perfumes (including microcapsules, macrocapsules, and perfume encapsulated in liposomes, vessicles, or microemulsions); chelants, such as ethylenediamine tetra-acetic acid; zeolites; activated silica, activated carbon granules or fibers; activated silica particulates; polycarboxylic acids, such as citric acid; cyclodextrins and cyclodextrin derivatives; chitosan or chitin and derivatives thereof; oxidizing agents; antimicrobial agents, including silver-loaded zeolites; triclosan; kieselguhr; and mixtures thereof. In addition to controlling odor from the body or body wastes, odor control strategies can also be employed to mask or control any odor of the treated substrate. Typically, the wetting composition contains less than about 5 weight percent of odor control additives based on the total weight of the wetting composition. In another aspect, the wetting composition contains from about 0.01 weight percent to about 2 weight percent of odor control additives. Yet, in another aspect, the wetting composition contains from about 0.03 weight percent to about 1 weight percent of odor control additives. In one embodiment of the present invention, the wetting composition and/or pre-moistened wipes comprise derivatized cyclodextrins, such as hydroxypropyl beta-cyclodextrin in solution, which remain on the skin after wiping and provide an odor-absorbing layer. In other embodiments, the odor source is removed or neutralized by application of an odor-control additive, exemplified by the action of a chelant that binds metal groups necessary for the function of many proteases and other enzymes that commonly produce an odor. Chelating the metal group interferes with the enzyme's action and decreases the risk of malodor in the product. Principles for the application of chitosan or chitin derivatives to nonwoven webs and cellulosic fibers are described by S. Lee et al. in "Antimicrobial and Blood Repellent Finishes for Cotton and Nonwoven Fabrics Based on Chitosan and Fluoropolymers," Textile Research Journal, 69(2); 104-112, February 1999.

If a binder is employed in the non-woven fabric, detackifying agents can be used in the wetting composition to reduce the tackiness of the binder. Suitable detackifiers include any substance known in the art to reduce tack between two adjacent fibrous sheets treated with an adhesive-like polymer or any substance capable of reducing the tacky feel of an adhesive-like polymer on the skin. Detackifiers can be applied as solid particles in dry form, as a suspension or as a slurry of particles. Deposition can be by spray, coating, electrostatic deposition, impingement, filtration (i.e., a pressure differential drives a particle-laden gas phase through the substrate, depositing particles by a filtration mechanism), and the like, and can be applied uniformly on one or more surfaces of the substrate or may be applied in a pattern (e.g., repeating or random patterns) over a portion of the surface or surfaces of the substrate. The detackifier can be present throughout the thickness of the substrate, but may be concentrated at one or both surfaces, and may be substantially only present on one or both surfaces of the substrate. Specific detackifiers include, but are not limited to, powders, such as talc powder, calcium carbonate, mica; starches, such as corn starch; *lycopodium* powder; mineral fillers, such as titanium dioxide; silica powder; alumina; metal oxides in general; baking powder; kieselguhr; and the like. Polymers and other additives having low surface energy may also be used, including a wide variety of fluorinated polymers, silicone additives, polyolefins and thermoplastics, waxes, debonding agents known in the paper industry including compounds having alkyl side chains such as those having 16 or more carbons, and the like. Compounds used as release agents for molds and candle making may also be considered, as well as, dry lubricants and fluorinated release agents.

The wetting composition of the present invention can be further modified by the addition of solid particulates or microparticulates. Suitable particulates include, but are not limited to, mica, silica, alumina, calcium carbonate, kaolin, talc, and zeolites. The particulates can be treated with stearic acid or other additives to enhance the attraction or bridging of the particulates to the binder system, if desired. Also, two-component microparticulate systems, commonly used as retention aids in the papermaking industry, can be used. Such two-component microparticulate systems generally comprise a colloidal particle phase, such as silica particles, and a water-soluble cationic polymer for bridging the particles to the fibers of the web to be formed. The presence of particulates in the wetting composition can serve one or more useful functions, such as (1) increasing the opacity of the pre-moistened wipes; (2) modifying the rheology or reducing the tackiness of the pre-moistened wipe; (3) improving the tactile properties of the wipe; or (4) delivering desired agents to the skin via a particulate carrier, such as a porous carrier or a microcapsule. Typically, the wetting composition contains less than about 25 weight percent of particulate based on the total weight of the wetting composition. In another aspect, the wetting composition contains from about 0.05 weight percent to about 10 weight percent of microparticulate. Yet, in another aspect, the wetting composition contains from about 0.1 weight percent to about 5 weight percent of microparticulate.

Microcapsules and other delivery vehicles can also be used in the wetting composition of the present invention to provide skin-care agents; medications; comfort promoting agents, such as eucalyptus; perfumes; skin care agents; odor control additives; vitamins; powders; and other additives to the skin of the user. For example, the wetting composition can contain up to about 25 weight percent of microcapsules or other delivery vehicles based on the total weight of the wetting composition. In another aspect, the wetting composition can contain from about 0.05 weight percent to about 10 weight percent of microcapsules or other delivery vehicles. Yet, in another aspect, the wetting composition can contain from about 0.2 weight percent to about 5.0 weight percent of microcapsules or other delivery vehicles.

Microcapsules and other delivery vehicles are well known in the art. For example, POLY-PORE® E200 (Chemdal Corp., Arlington Heights, EL), is a delivery agent comprising soft, hollow spheres that can contain an additive at over 10 times the weight of the delivery vehicle. Known additives reported to have been used with POLY-PORE® E200 include, but are not limited to, benzoyl peroxide, salicylic acid, retinol, retinol palmitate, octyl methoxycinnamate, tocopherol, silicone compounds (DC 435), and mineral oil. Another delivery vehicle which can be employed with non-woven fabric is a sponge-like material marketed as POLY-PORE® L200, which is reported to have been used with silicone (DC 435) and mineral oil. Other known delivery systems include cyclodextrins and their derivatives, liposomes, polymeric sponges, and spray-dried starch. Additives present in microcapsules are isolated from the environment and the other agents in the wetting composition until the wipe is applied to the skin, whereupon the microcapsules break and deliver their load to the skin or other surfaces.

The wetting composition of the present invention can contain preservatives and/or anti-microbial agents. Several preservatives and/or anti-microbial agents useful in the present invention include, but are not limited to, Mackstat H 66 (available from McIntyre Group, Chicago, Ill.), DMDM hydantoin (e.g., Glydant Plus™, Lonza, Inc., Fair Lawn, N.J.), iodopropynyl butylcarbamate, Kathon (Rohm and Hass, Philadelphia, Pa.), methylparaben, propylparaben, 2-bromo-2-nitropropane-1,3-diol, benzoic acid, and the like. Typically, the wetting composition contains less than about 2 weight percent on an active basis of preservatives and/or antimicrobial agents based on the total weight of the wetting composition. In another aspect, the wetting composition contains from about 0.01 weight percent to about 1 weight percent of preservatives and/or anti-microbial agents. Yet, in another aspect, the wetting composition contains from about 0.01 weight percent to about 0.5 weight percent of preservatives and/or anti-microbial agents.

A variety of wetting agents and/or cleaning agents can be used in the wetting composition of the present invention. Suitable wetting agents and/or cleaning agents include, but are not limited to, detergents and nonionic, amphoteric, and anionic surfactants, especially amino acid-based surfactants. Amino acid-based surfactant systems, such as those derived from amino acids L-glutamic acid and other natural fatty acids, offer pH compatibility to human skin and good cleansing power, while being relatively safe and providing improved tactile and moisturization properties compared to other anionic surfactants. One function of the surfactant is to improve wetting of the dry substrate with the wetting composition. Another function of the surfactant can be to disperse bathroom soils when the pre-moistened wipe contacts a soiled area and to enhance their absorption into the substrate. The surfactant can further assist in make-up removal, general personal cleansing, hard surface cleansing, odor control, and the like. One commercial example of an amino-acid based surfactant is acylglutamate, marketed under the Amisoft name by Ajinomoto Corp., Tokyo, Japan. Typically, the wetting composition contains less than about 3 weight percent of wetting agents and/or cleaning agents based on the total weight of the wetting composition. In another aspect, the wetting composition contains from about 0.01 weight percent to about 2 weight percent of wetting agents and/or cleaning agents. Yet, in another aspect, the wetting composition contains from about 0.1 weight percent to about 0.5 weight percent of wetting agents and/or cleaning agents.

In addition to amino-acid based surfactants, a wide variety of surfactants can be used in the present invention. Suitable non-ionic surfactants include, but are not limited to, the condensation products of ethylene oxide with a hydrophobic (oleophilic) polyoxyalkylene base formed by the condensation of propylene oxide with propylene glycol. The hydrophobic portion of these compounds desirably has a molecular weight sufficiently high so as to render it water-insoluble. The addition of polyoxyethylene moieties to this hydrophobic portion increases the water-solubility of the molecule as a whole, and the liquid character of the product is retained up to the point where the polyoxyethylene content is about 50% of the total weight of the condensation product. Examples of compounds of this type include commercially-available Pluronic surfactants (BASF Wyandotte Corp.), such as those in which the polyoxypropylene ether has a molecular weight of about 1500-3000 and the polyoxyethylene content is about 35-55% of the molecule by weight, i.e. Pluronic L-62.

Other useful nonionic surfactants include, but are not limited to, the condensation products of $C_8$-$C_{22}$ alkyl alcohols with 2-50 moles of ethylene oxide per mole of alcohol. Examples of compounds of this type include the condensation products of Cii-Cis secondary alkyl alcohols with 3-50 moles of ethylene oxide per mole of alcohol, which are commercially-available as the Poly-Tergent SLF series from Olin Chemicals or the TERGITOL® series from Union Carbide, i.e. TERGITOL® 25-L-7, which is formed by condensing about 7 moles of ethylene oxide with a $Cj_2$-$C_{15}$ alkanol.

Other nonionic surfactants, which can be employed in the wetting composition of the present invention, include the ethylene oxide esters of $C_6$-$Ct_2$ alkyl phenols such as (nonylphenoxy)polyoxyethylene ether. Particularly useful are the esters prepared by condensing about 8-12 moles of ethylene oxide with nonylphenol, i.e. the IGEPAL® CO series (GAF Corp.). Further non-ionic surface active agents include, but are not limited to, alkyl polyglycosides (APG), derived as a condensation product of dextrose (D-glucose) and a straight or branched chain alcohol. The glycoside portion of the surfactant provides a hydrophile having high hydroxyl density, which enhances water solubility. Additionally, the inherent stability of the acetal linkage of the glycoside provides chemical stability in alkaline systems. Furthermore, unlike some non-ionic surface active agents, alkyl polyglycosides have no cloud point, allowing one to formulate without a hydrotrope, and these are very mild, as well as readily biodegradable non-ionic surfactants. This class of surfactants is available from Horizon Chemical under the trade names of APG-300, APG-350, APG-500, and APG-500.

Silicones are another class of wetting agents available in pure form, or as microemulsions, macroemulsions, and the like. One exemplary non-ionic surfactant group is the silicone-glycol copolymers. These surfactants are prepared by adding poly(lower)alkylenoxy chains to the free hydroxyl groups of dimethylpolysiloxanols and are available from the Dow Corning Corp as Dow Corning 190 and 193 surfactants (CTFA name: dimethicone copolyol). These surfactants function, with or without any volatile silicones used as solvents, to control foaming produced by the other surfactants, and also impart a shine to metallic, ceramic, and glass surfaces.

Anionic surfactants can be used in the wetting compositions of the present invention. Anionic surfactants are useful due to their high detergency include anionic detergent salts having alkyl substituents of 8 to 22 carbon atoms such as the water-soluble higher fatty acid alkali metal soaps, e.g., sodium myristate and sodium palmitate. A preferred class of anionic surfactants encompasses the water-soluble sulfated and sulfonated anionic alkali metal and alkaline earth metal detergent salts containing a hydrophobic higher alkyl moiety (typically containing from about 8 to 22 carbon atoms) such as salts of higher alkyl mono or polynuclear aryl sulfonates having from about 1 to 16 carbon atoms in the alkyl group, with examples available as the Bio-Soft series, i.e. Bio-Soft D-40 (Stepan Chemical Co.).

Other useful classes of anionic surfactants include, but are not limited to, the alkali metal salts of alkyl naphthalene sulfonic acids (methyl naphthalene sodium sulfonate, Petro AA, Petrochemical Corporation); sulfated higher fatty acid monoglycerides such as the sodium salt of the sulfated monoglyceride of cocoa oil fatty acids and the potassium salt of the sulfated monoglyceride of tallow fatty acids; alkali metal salts of sulfated fatty alcohols containing from about 10 to 18 carbon atoms (e.g., sodium lauryl sulfate and sodium stearyl sulfate); sodium $C_{14}$-$C_{16}$-alphaolefin sulfonates such as the Bio-Terge series (Stepan Chemical Co.); alkali metal salts of sulfated ethyleneoxy fatty alcohols (the sodium or ammonium sulfates of the condensation products of about 3 moles of ethylene oxide with a $C_{12}$-$C_{15}$ n-alkanol, i.e., the Neodol ethoxysulfates, Shell Chemical Co.); alkali metal salts of higher fatty esters of low molecular weight alkylol sulfonic acids, e.g. fatty acid esters of the sodium salt of isothionic acid, the fatty ethanolamide sulfates; the fatty acid amides of amino alkyl sulfonic acids, e.g. lauric acid amide of taurine; as well as numerous other anionic organic surface active agents such as sodium xylene sulfonate, sodium naphthalene sulfonate, sodium toulene sulfonate and mixtures thereof.

A further useful class of anionic surfactants includes the 8-(4-n-alkyl-2-cyclohexenyl)-octanoic acids, wherein the cyclohexenyl ring is substituted with an additional carboxylic acid group. These compounds or their potassium salts, are commercially-available from Westvaco Corporation as Diacid 1550 or H-240. In general, these anionic surface active agents can be employed in the form of their alkali metal salts, ammonium or alkaline earth metal salts.

The wetting composition can further comprise an aqueous microemulsion of silicone particles. For example, U.S. Pat. No. 6,037,407, which is incorporated herein in its entirety by reference, describes organopolysiloxanes in an aqueous microemulsion. Typically, the wetting composition contains less than about 5 weight percent of a microemulsion of silicone particles based on the total weight of the wetting composition. In another aspect, the wetting composition contains from about 0.02 weight percent to about 3 weight percent of a microemulsion of silicone particles. Yet, in another aspect, the wetting composition contains from about 0.02 weight percent to about 0.5 weight percent of a microemulsion of silicone particles.

Silicone emulsions in general can be applied to the pre-moistened wipe by any known coating method. For example, the pre-moistened wipe may be moistened with a wetting composition comprising a water-dispersible or water-miscible, silicone-based component. Further, the wipe can comprise a nonwoven web of fibers having a water-dispersible binder, wherein the web is moistened with a lotion comprising a silicone-based sulfosuccinate. The silicone-based sulfosuccinate provides gentle and effective cleansing without a high level of surfactant. Additionally, the silicone-based sulfosuccinate provides a solubilization function, which prevents precipitation of oil-soluble components, such as fragrance components, vitamin extracts, plant extracts, and essential oils.

In one embodiment of the present invention, the wetting composition comprises a silicone copolyol sulfosuccinate, such as disodium dimethicone copolyol sulfosuccinate and diammonium dimethicone copolyolsulfosuccinate. In one aspect, the wetting composition comprises less than about 2 percent by weight of the silicone-based sulfosuccinate, and, in another aspect, from about 0.05 percent to about 0.30 percent by weight of the silicone-based sulfosuccinate.

In another example of a product comprising a silicone emulsions, Dow Corning 9506 powder can be present in the wetting composition. Dow Corning 9506 powder is believed to comprise a dimethicone/vinyldimethicone cross-polymer and is a spherical powder, which is said to be useful in controlling skin oils (see "New Chemical Perspectives," Soap and Cosmetics, Vol. 76, No. 3, March 2000, p. 12). Thus, a water-dispersible wipe, which delivers a powder effective in controlling skin oil, is also within the scope of the present invention. Principles for preparing silicone emulsions are disclosed in WO 97/10100.

The wetting composition of the present invention can contain one or more emollients. Suitable emollients include, but are not limited to, PEG 75 lanolin, methyl gluceth 20 benzoate, $C_{12}$-$C_{15}$ alkyl benzoate, ethoxylated cetyl stearyl alcohol, products marketed as Lambent wax WS-L, Lambent WD-F, Cetiol HE (Henkel Corp.), Glucam P20 (Amerchol), Polyox WSR N-10 (Union Carbide), Polyox WSR N-3000 (Union Carbide), Luviquat (BASF), Finsolv SLB 101 (Finetex Corp.), mink oil, allantoin, stearyl alcohol, Estol 1517 (Unichema), and Finsolv SLB 201 (Finetex Corp.).

An emollient can also be applied to a surface of the non-woven fabric prior to or after wetting with the wetting composition. Such an emollient can be insoluble in the wetting composition and can be immobile except when exposed to a force. For example, a petrolatum-based emollient can be applied to one surface in a pattern, after which the other surface is wetted to saturate the wipe. Such a product could provide a cleaning surface and an opposing skin treatment surface.

The emollient composition in such products and other products of the present invention can comprise a plastic or fluid emollient such as one or more liquid hydrocarbons (e.g., petrolatum), mineral oil and the like, vegetable and animal fats (e.g., lanolin, phospholipids and their derivatives) and/or a silicone materials such as one or more alkyl substituted polysiloxane polymers, including the polysiloxane emollients disclosed in U.S. Pat. No. 5,891,126, which is incorporated herein in its entirety by reference. Optionally, a hydrophilic surfactant can be combined with a plastic emollient to improve wettability of the coated surface. In some embodiments of the present invention, it is contemplated that liquid hydrocarbon emollients and/or alkyl substituted polysiloxane polymers may be blended or combined with one or more fatty acid ester emollients derived from fatty acids or fatty alcohols.

In an embodiment of the present invention, the emollient material is in the form of an emollient blend. For example, the emollient blend can comprise a combination of one or more liquid hydrocarbons (e.g., petrolatum), mineral oil and the like, vegetable and animal fats (e.g., lanolin, phospholipids and their derivatives), with a silicone material such as one or more alkyl substituted polysiloxane polymers. In another aspect, the emollient blend comprises a combination of liquid hydrocarbons (e.g., petrolatum) with dimethicone or with dimethicone and other alkyl substituted polysiloxane polymers. In some embodiments of the present invention, it is contemplated that blends of liquid hydrocarbon emollients and/or alkyl substituted polysiloxane polymers may be blended with one or more fatty acid ester emollients derived from fatty acids or fatty alcohols. PEG-7 glyceryl cocoate, available as Standamul HE (Henkel Corp., Hoboken, N.J), can also be considered.

Water-soluble, self-emulsifying emollient oils, which are useful in the present wetting compositions, include the polyoxyalkoxylated lanolins and the polyoxyalkoxylated fatty alcohols, as disclosed in U.S. Pat. No. 4,690,821, which is incorporated herein in its entirety by reference. The polyoxyalkoxy chains comprise mixed propylenoxy and ethyleneoxy units. The lanolin derivatives typically comprise about 20-70 such lower-alkoxy units while the $C_{12}$-$C_{20}$-fatty alcohols will be derivatized with about 8-15 lower-alkyl units. One such useful lanolin derivative is Lanexol AWS (PPG-12-PEG-50, Croda, Inc., New York, N.Y.). A useful poly(15-20)$C_2$-$C_3$-alkoxylate is PPG-5-Ceteth-20, known as Procetyl AWS (Croda, Inc.).

Typically, the wetting composition contains less than about 25 weight percent of emollients based on the total weight of the wetting composition. In another aspect, the wetting composition can comprise less than about 5 weight percent emollient, and, in yet another aspect, less than about 2% emollient. Still, in another aspect, the wetting composition can contain from about 0.01 weight percent to about 8 weight percent of emollients. Yet still, in another aspect, the wetting composition can contain from about 0.2 weight percent to about 2 weight percent of emollients.

In one embodiment, the wetting composition and/or pre-moistened wipes of the present invention comprise an oil-in-water emulsion comprising an oil phase containing at least one emollient oil and at least one emollient wax stabilizer dispersed in an aqueous phase comprising at least one polyhydric alcohol emollient and at least one organic water-soluble detergent, as disclosed in U.S. Pat. No. 4,559,157, the entirety of which is herein incorporated by reference.

Surface feel modifiers can be employed with the non-woven fabric of the present invention to improve the tactile sensation (e.g., lubricity) of the skin during use of the product. Suitable surface feel modifiers include, but are not limited to, commercial debonders; and softeners, such as the softeners used in the art of tissue making including quaternary ammonium compounds with fatty acid side groups, silicones, waxes, and the like. Exemplary quaternary ammonium compounds with utility as softeners are disclosed in U.S. Pat. No. 3,554,862; U.S. Pat. No. 4,144,122; U.S. Pat. No. 5,573,637; and U.S. Pat. No. 4,476,323, the entirety of all of which is herein incorporated by reference. Typically, the wetting composition contains less than about 2 weight percent of surface feel modifiers based on the total weight of the wetting composition. In another aspect, the wetting composition contains from about 0.01 weight percent to about 1 weight percent of surface feel modifiers. Yet, in another aspect, the wetting composition contains from about 0.01 weight percent to about 0.05 weight percent of surface feel modifiers.

A variety of fragrances can be used in the wetting composition of the present invention. Typically, the wetting composition contains less than about 2 weight percent of fragrances based on the total weight of the wetting composition. In another aspect, the wetting composition contains from about 0.01 weight percent to about 1 weight percent of fragrances. Yet, in another aspect, the wetting composition contains from about 0.01 weight percent to about 0.05 weight percent of fragrances.

Further, a variety of fragrance solubilizers can be used in the wetting composition of the present invention. Suitable fragrance solubilizers include, but are not limited to, polysorbate 20, propylene glycol, ethanol, isopropanol, diethylene glycol monoethyl ether, dipropylene glycol, diethyl phthalate, triethyl citrate, Ameroxol OE-2 (Amerchol Corp.), Brij 78 and Brij 98 (ICI Surfactants), Arlasolve 200 (ICI Surfactants), Calfax 16L-35 (Pilot Chemical Co.), Capmul POE-S (Abitec Corp.), Finsolv SUBSTANTIAL (Finetex), and the like. Typically, the wetting composition contains less than about 2 weight percent of fragrance solubilizers based on the total weight of the wetting composition. In another aspect, the wetting composition contains from about 0.01 weight percent to about 1 weight percent of fragrance solubilizers. Yet, in another aspect, the wetting composition contains from about 0.01 weight percent to about 0.05 weight percent of fragrance solubilizers.

Opacifers can be employed in the wetting composition. Suitable opacifiers include, but are not limited to, titanium dioxide or other minerals or pigments, and synthetic opacifiers such as REACTOPAQUE® particles (available from Sequa Chemicals, Inc., Chester, S.C.). Typically, the wetting composition contains less than about 2 weight percent of opacifiers based on the total weight of the wetting composition. In another aspect, the wetting composition contains from about 0.01 weight percent to about 1 weight percent of opacifiers. Yet, in another aspect, the wetting composition contains from about 0.01 weight percent to about 0.05 weight percent of opacifiers.

Suitable pH control agents for use in the wetting composition of the present invention include, but are not limited to, malic acid, citric acid, hydrochloric acid, acetic acid, sodium hydroxide, potassium hydroxide, and the like. An appropriate pH range minimizes the amount of skin irritation resulting from the wetting composition on the skin. Typically, the pH range of the wetting composition is from about 3.5 to about 6.5. In another aspect, the pH range of the wetting composition is from about 4 to about 6. Sill, in another aspect, the wetting composition contains less than about 2 weight percent of a pH adjuster based on the total weight of the wetting composition. In another aspect, the wetting composition contains from about 0.01 weight percent to about 1 weight percent of a pH adjuster. Yet, in another aspect, the wetting composition contains from about 0.01 weight percent to about 0.05 weight percent of a pH adjuster.

A variety of wetting compositions, formed from one or more of the above-described components, can be used with the wet wipes of the present invention.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, various modifications may be made of the invention without departing from the scope thereof and it is desired, therefore, that only such limitations shall be placed thereon as are imposed by the prior art and which are set forth in the appended claims.

TABLE 2

Physical Properties of Carded/Hydroentangled Fabrics

| | 100% Rayon (Control) | 100% Hemp | 60% Rayon 40% PET (Control) | 60% Hemp 40% PET | 80% Hemp 20% PET | 60% Hemp 40% PET Apertured | 80% Hemp 20% PET Apertured |
|---|---|---|---|---|---|---|---|
| Basis Wt (gsm) | 108.9 | 153.3 | 124.9 | 85.7 | 99.0 | 126.1 | 90.4 |
| Caliper (mils/4 ply) | 105.7 | 135 | 107.3 | 106.3 | 115.4 | 193.6 | 159.9 |
| MD Dry Tensile (g/3") | 24010 | 15390 | 25890 | 13770 | 14790 | 16650 | 7800 |
| MD Dry Stretch (%) | 33.2 | 31.0 | 53.0 | 49.25 | 38.9 | 84.4 | 52.0 |
| CD Wet Tensile (g/3") | 25075 | 27150 | 50490 | 27120 | 31410 | 55890 | 20490 |
| Absorbency Rate (sec.) | 1.7 | 2.2 | 2.8 | 3.4 | 2.3 | 4.9 | 2.7 |
| Absorbency Capacity (g/g) | 6.8 | 5.6 | 6.2 | 7.4 | 7.1 | 9.7 | 10.7 |
| Brightness (%) | 84.52 | 72.12 | 87.72 | 77.65 | 74.01 | 75.87 | 71.73 |

TABLE 3

Physical Properties of Hemp and Flax Wipe Inventive Substrate in Comparison to Conventional Wipe Substrates

| | | Heavy Duty Shop Towel Wipe Substrates | | | | Food Service Towel Substrates | |
|---|---|---|---|---|---|---|---|
| | | Inventive Wiper | | Competitive Wipers | | Inventive | |
| Property Explanation | Property | Cell 4 100% Hemp Herringbone Pattern | Cell 10 100% Flax Herringbone Pattern | Woven Cotton/PET Shop Towel | K-C Wypall X-80 HEF/Pulp/PP | Wiper Cell 8 100% Flax Apertured | Competitive Wipers Chix ® 8250 |
| Basis Weight | Basis Weight (gsm) | 114 | 116 | 197 | 113 | 76 | 65.7 |
| Thickness | Caliper (mils/8 ply) | 213 | 286 | 346 | 183 | 227 | 164 |
| Strength | MD Dry Tensile (g/1 inch) | 5744 | 7221 | 8287 | 5740 | 4681 | 4214 |
| Strength | MD Wet Tensile (g/1 inch) | 6021 | 7421 | 8294 | 4434 | 4842 | 4181 |
| Strength | CD Wet Tensile (g/1 inch) | 2333 | 3347 | 8871 | 2971 | 2115 | 3769 |
| Strength | Root Mean Wet MD-CD Tensile (g/1 inch) | 3748 | 4984 | 8578 | 3630 | 3200 | 3970 |
| Strength | Root Mean MD-CD TEA (g/mm) | 20 | 42.9 | TBD | 36 | 21.8 | 38.9 |
| Grams of water absorbed per gram of wipe | Water Absorb Capacity (g/g) | 7.0 | 5.8 | 2.8 | 6.2 | 7.8 | 9.2 |
| Grams of oil absorbed per gram of wipe | Motor Oil Hold Capacity (g/g) | 5.6 | 5.9 | 5.7 | 4.9 | 7.4 | 8.3 |
| Grams of oil absorbed per m2 of wipe | Motor Oil Hold Capacity (g/m2) | 638.4 | 685 | 1123 | 554 | 561 | 545 |
| Abrasion resistance/durability when wet | Stoll Abrasion Wet (# strokes) | 50 | 59 | TBD | 84 | 35 | 37 |
| Lint loss when rubbed dry against cloth | Dry Lint (mg/m^2) | 64 | 49.3 | TBD | 44 | 78.9 | 19.7 |

TABLE 3-continued

Physical Properties of Hemp and Flax Wipe Inventive Substrate in Comparison to Conventional Wipe Substrates

| | | Heavy Duty Shop Towel Wipe Substrates | | | | Food Service Towel Substrates | |
|---|---|---|---|---|---|---|---|
| | | Inventive Wiper | | Competitive Wipers | | Inventive | |
| Property Explanation | Property | Cell 4 100% Hemp Herringbone Pattern | Cell 10 100% Flax Herringbone Pattern | Woven Cotton/PET Shop Towel | K-C Wypall X-80 HEF/Pulp/ PP | Wiper Cell 8 100% Flax Apertured | Competitive Wipers Chix ® 8250 |
| Lint loss in water | Wet Extracted Lint (%) | 0.27 | 0.12 | TBD | 0.07 | 0.04 | 0.05 |

TABLE 4

Physical Properties and Relative Pectin Content of Inventive Fabrics

| Test | Batch 1 Herringbone Pattern (100% Hemp Bast Fiber) | Batch 2 Herringbone Pattern (100% Hemp Bast Fiber) | Batch 3 Herringbone Pattern (100% Hemp Bast Fiber) |
|---|---|---|---|
| Reduced Sugar Content from Pectin Extraction (%) | 0.1 | 0.3 | 0.6 |
| Basis Weight (gsm) | 138.1 | 114.5 | 110.2 |
| MD Dry Tensile Strength (g/inch) | 9570 | 2490 | 1480 |
| CD Dry Tensile Strength (g/inch) | 1790 | 370 | 220 |
| MD/CD Dry Ratio | 5.3 | 6.7 | 6.7 |
| MD Wet Tensile Strength (g/inch) | 8720 | 1370 | 1440 |
| CD Wet Tensile Strength (g/inch) | 2210 | 230 | 200 |
| MD/CD Wet Ratio | 3.9 | 6.0 | 7.2 |

What is claimed is:

1. A nonwoven fabric comprising a majority of full length natural individualized fibers which are substantially straight, plant-based, smooth and elongated, and substantially pectin-free and have a mean length greater than 6 millimeters (mm).

2. The nonwoven fabric of claim 1, wherein the substantially straight, plant-based, smooth and elongated, substantially pectin-free fibers are bast fibers.

3. The nonwoven fabric of claim 1, wherein the substantially straight, plant-based, smooth and elongated, substantially pectin-free fibers are fibers extracted from flax, hemp, jute, ramie, nettle, Spanish broom, kenaf plants, or any combination thereof.

4. The nonwoven fabric of claim 1, wherein the substantially straight, plant-based, smooth and elongated, substantially pectin-free fibers have less than 10% by weight of the pectin content of the naturally occurring fibers from which the substantially pectin-free fibers are derived.

5. The nonwoven fabric of claim 1, wherein the substantially straight, plant-based, smooth and elongated, substantially pectin-free fibers have less than 15% by weight of the pectin content of the naturally occurring fibers from which the substantially pectin-free fibers are derived.

6. The nonwoven fabric of claim 1, wherein the substantially straight, plant-based, smooth and elongated, substantially pectin-free fibers have less than 20% by weight of the pectin content of the naturally occurring fibers from which the substantially pectin-free fibers are derived.

7. The nonwoven fabric of claim 1, wherein the substantially straight, plant-based, smooth and elongated, substantially pectin-free fibers have a mean length of at least 7 mm.

8. The nonwoven fabric of claim 1, wherein the substantially straight, plant-based, smooth and elongated, substantially pectin-free fibers have a mean length of at least 8 mm.

9. The nonwoven fabric of claim 1, wherein the substantially straight, plant-based, smooth and elongated, substantially pectin-free fibers have a mean length of at least 9 mm.

10. The nonwoven fabric of claim 1, wherein the substantially straight, plant-based, smooth and elongated, substantially pectin-free fibers have a mean length of at least 10 mm.

11. The nonwoven fabric of claim 1, wherein the substantially straight, plant-based, smooth and elongated, substantially pectin-free fibers have a mean length greater than 12 mm.

12. The nonwoven fabric of claim 1, further comprising crimped or straight staple fibers.

13. The nonwoven fabric of claim 1, further comprising crimped or straight man-made cellulosic fibers, thermoplastic fibers, or any combination thereof.

14. The nonwoven fabric of claim 1, wherein the nonwoven fabric is a wet wiper, a dry wiper, an impregnated wiper, a sorbent, a medical supply product, a personal protective fabric, an automotive protective covering, a personal care article, a fluid filtration product, a home furnishing product, a thermal insulation product, an acoustic insulation product, an agricultural application product, a landscaping application product, or a geotextile application product.

15. The nonwoven fabric of claim 1, wherein the nonwoven fabric is a baby wipe, a cosmetic wipe, a perinea wipe, a disposable washcloth, a kitchen wipe, a bath wipe, a hard surface wipe, a glass wipe, a mirror wipe, a leather wipe, an electronics wipe, a lens wipe, a polishing wipe, a medical cleaning wipe, a disinfecting wipe, a surgical drape, a surgical gown, a wound care product, a protective coverall, a sleeve protector, a diaper, a feminine care article, a nursing pad, an air filter, a water filter, an oil filter, or a furniture backing.

16. The nonwoven fabric of claim 1, wherein the nonwoven fabric has thermoplastic fibers substantially dispersed among the individualized fibers and the nonwoven fabric has a pattern present on at least one surface.

17. A method of making the nonwoven fabric of claim 1, the method comprising:
 chemically treating naturally occurring fibers to substantially remove pectin and form substantially individualized fibers;

carding the substantially individualized fibers to form a randomly arrayed fiber web; and bonding the randomly arrayed fiber web to form the nonwoven fabric.

18. The method of claim 17, further comprising adding thermoplastic fibers to the individualized fibers and thermal bonding the nonwoven fabric.

19. The method of claim 17, wherein bonding is hydroentangling.

20. The method of claim 17, wherein bonding is mechanical needle punching.

21. The method of claim 17, wherein bonding is passing a heated air stream through the web.

22. A laminate comprising the nonwoven fabric of claim 1, a film, and an adhesive disposed between the fabric and the film.

23. The laminate of claim 22, wherein the film comprises a polyethylene polymer, a polyethylene copolymer, a polypropylene polymer, a polypropylene copolymer, a polyurethane polymer, a polyurethane copolymer, or a styrenebutadiene copolymer.

24. The laminate of claim 22, wherein the film comprises linear low density polyethylene.

25. The laminate of claim 22, wherein the adhesive is a sprayable latex, a polyalphaolefin, or an ethylene vinyl acetate.

26. The laminate of claim 22, wherein the film is a breathable film.

27. A method of making the laminate of claim 22, the method comprising:

chemically treating naturally occurring fibers bundled with pectin to substantially remove pectin and form substantially individualized fibers;

carding the substantially individualized fibers to form a randomly arrayed fiber web;

bonding the randomly arrayed fiber web to form the nonwoven fabric having a support surface;

disposing the adhesive onto either the support surface of the nonwoven fabric or a surface of the film;

disposing the film onto the support surface of the nonwoven fabric; and nipping to form the laminate.

28. The method of claim 27, wherein the film comprises a polyethylene polymer, a polyethylene copolymer, a polypropylene polymer, a polypropylene copolymer, a polyurethane polymer, a polyurethane copolymer, or a styrenebutadiene copolymer.

29. The method of claim 27, wherein the film comprises linear low density polyethylene.

30. The method of claim 27, wherein the adhesive is a sprayable latex, a polyalphaolefin, or an ethylene vinyl acetate.

31. A laminate comprising a first nonwoven fabric and another fabric bonded to the first nonwoven fabric, the first nonwoven fabric being the nonwoven fabric of claim 1, the another fabric being at least one of a second nonwoven fabric or a woven fabric, the second nonwoven fabric optionally being an additional nonwoven fabric of claim 1.

32. The laminate of claim 31, wherein the another fabric is bonded to the first nonwoven fabric with an adhesive.

33. A nonwoven fabric comprising a majority of full length natural individualized fibers which are substantially straight, non-cotton, plant-based, smooth and elongated, and substantially pectin-free and are un-cut with a distribution of fiber lengths and a mean length greater than 10 mm.

34. The nonwoven fabric of claim 33, wherein the non-cotton, plant-based, smooth and elongated, and substantially pectin-free fibers are bast fibers.

35. The nonwoven fabric of claim 33, further comprising crimped or straight staple fibers.

36. The nonwoven fabric of claim 33, wherein the non-cotton, plant-based, smooth and elongated, and substantially pectin-free fibers are fibers extracted from flax, hemp, jute, ramie, nettle, Spanish broom, kenaf plants, or any combination thereof.

37. The nonwoven fabric of claim 33, wherein the non-cotton, plant-based, smooth and elongated, and substantially pectin-free fibers have less than 10% by weight of the pectin content of the naturally occurring fibers from which the substantially pectin-free fibers are derived.

38. The nonwoven fabric of claim 33, wherein the non-cotton, plant-based, smooth and elongated, and substantially pectin-free fibers have less than 15% by weight of the pectin content of the naturally occurring fibers from which the substantially pectin-free fibers are derived.

39. The nonwoven fabric of claim 33, wherein the non-cotton, plant-based, smooth and elongated, and substantially pectin-free fibers have less than 20% by weight of the pectin content of the naturally occurring fibers from which the substantially pectin-free fibers are derived.

40. The nonwoven fabric of claim 33, wherein the non-cotton, plant-based, smooth and elongated, and substantially pectin-free fibers have a mean length greater than 12 mm.

41. The nonwoven fabric of claim 33, further comprising crimped or straight man-made cellulosic fibers, thermoplastic fibers, or any combination thereof.

42. The nonwoven fabric of claim 33, wherein the nonwoven fabric is a wet wiper, a dry wiper, an impregnated wiper, a sorbent, a medical supply product, a personal protective fabric, an automotive protective covering, a personal care article, a fluid filtration product, a home furnishing product, a thermal insulation product, an acoustic insulation product, an agricultural application product, a landscaping application product, or a geotextile application product.

43. The nonwoven fabric of claim 33, wherein the nonwoven fabric is a baby wipe, a cosmetic wipe, a perinea wipe, a disposable washcloth, a kitchen wipe, a bath wipe, a hard surface wipe, a glass wipe, a mirror wipe, a leather wipe, an electronics wipe, a lens wipe, a polishing wipe, a medical cleaning wipe, a disinfecting wipe, a surgical drape, a surgical gown, a wound care product, a protective coverall, a sleeve protector, a diaper, a feminine care article, a nursing pad, an air filter, a water filter, an oil filter, or a furniture backing.

44. The nonwoven fabric of claim 33, wherein the nonwoven fabric has thermoplastic fibers substantially dispersed among the individualized fibers and the nonwoven fabric has a pattern present on at least one surface.

45. A method of making the nonwoven fabric of claim 33, the method comprising:

chemically treating naturally occurring fibers to substantially remove pectin and form substantially individualized fibers;

carding the substantially individualized fibers to form a randomly arrayed fiber web; and bonding the randomly arrayed fiber web to form the nonwoven fabric.

46. The method of claim 45, further comprising adding thermoplastic fibers to the individualized fibers and thermal bonding the nonwoven fabric.

47. The method of claim 45, wherein bonding is hydroentangling.

48. The method of claim 45, wherein bonding is mechanical needle punching.

49. The method of claim 45, wherein bonding is passing a heated air stream through the web.

50. A laminate comprising the nonwoven fabric of claim 33, a film, and an adhesive disposed between the fabric and the film.

51. The laminate of claim 50, wherein the film comprises a polyethylene polymer, a polyethylene copolymer, a polypropylene polymer, a polypropylene copolymer, a polyurethane polymer, a polyurethane copolymer, or a styrenebutadiene copolymer.

52. The laminate of claim 50, wherein the film comprises linear low density polyethylene.

53. The laminate of claim 50, wherein the adhesive is a sprayable latex, a polyalphaolefin, or an ethylene vinyl acetate.

54. The laminate of claim 50, wherein the film is a breathable film.

55. A method of making the laminate of claim 50, the method comprising:
chemically treating naturally occurring fibers bundled with pectin to substantially remove pectin and form substantially individualized fibers;
carding the substantially individualized fibers to form a randomly arrayed fiber web;
bonding the randomly arrayed fiber web to form the nonwoven fabric having a support surface;
disposing the adhesive onto either the support surface of the nonwoven fabric or a surface of the film;
disposing the film onto the support surface of the nonwoven fabric; and
nipping to form the laminate.

56. A laminate comprising a first nonwoven fabric and another fabric bonded to the first nonwoven fabric, the first nonwoven fabric being the nonwoven fabric of claim 33, the another fabric being at least one of a second nonwoven fabric or a woven fabric, the second nonwoven fabric optionally being an additional nonwoven fabric of claim 33.

57. The laminate of claim 56, wherein the another fabric is bonded to the first nonwoven fabric with an adhesive.

58. A nonwoven fabric comprising a majority of full length natural individualized fibers which are substantially straight, plant-based, smooth and elongated, and have a mean length greater than 10 mm.

59. The nonwoven fabric of claim 58, further comprising crimped or straight staple fibers.

60. The nonwoven fabric of claim 58, further comprising crimped or straight man-made cellulosic fibers, thermoplastic fibers, or any combination thereof.

61. The nonwoven fabric of claim 58, wherein the nonwoven fabric is a wet wiper, a dry wiper, an impregnated wiper, a sorbent, a medical supply product, a personal protective fabric, an automotive protective covering, a personal care article, a fluid filtration product, a home furnishing product, a thermal insulation product, an acoustic insulation product, an agricultural application product, a landscaping application product, or a geotextile application product.

62. The nonwoven fabric of claim 58, wherein the nonwoven fabric is a baby wipe, a cosmetic wipe, a perinea wipe, a disposable washcloth, a kitchen wipe, a bath wipe, a hard surface wipe, a glass wipe, a mirror wipe, a leather wipe, an electronics wipe, a lens wipe, a polishing wipe, a medical cleaning wipe, a disinfecting wipe, a surgical drape, a surgical gown, a wound care product, a protective coverall, a sleeve protector, a diaper, a feminine care article, a nursing pad, an air filter, a water filter, an oil filter, or a furniture backing.

63. The nonwoven fabric of claim 58, wherein the nonwoven fabric has thermoplastic fibers substantially dispersed among the individualized fibers and the nonwoven fabric has a pattern present on at least one surface.

64. A method of making the nonwoven fabric of claim 58, the method comprising:
chemically treating naturally occurring fibers to substantially remove pectin and form substantially individualized fibers;
carding the substantially individualized fibers to form a randomly arrayed fiber web; and
bonding the randomly arrayed fiber web to form the nonwoven fabric.

65. The method of claim 64, further comprising adding thermoplastic fibers to the individualized fibers and thermal bonding the nonwoven fabric.

66. The method of claim 64, wherein bonding is hydroentangling.

67. The method of claim 64, wherein bonding is mechanical needle punching.

68. The method of claim 64, wherein bonding is passing a heated air stream through the web.

69. A laminate comprising the nonwoven fabric of claim 58, a film, and an adhesive disposed between the fabric and the film.

70. The laminate of claim 69, wherein the film comprises a polyethylene polymer, a polyethylene copolymer, a polypropylene polymer, a polypropylene copolymer, a polyurethane polymer, a polyurethane copolymer, or a styrenebutadiene copolymer.

71. The laminate of claim 69, wherein the film comprises linear low density polyethylene.

72. The laminate of claim 69, wherein the adhesive is a sprayable latex, a polyalphaolefin, or an ethylene vinyl acetate.

73. The laminate of claim 69, wherein the film is a breathable film.

74. A method of making the laminate of claim 69, the method comprising:
chemically treating naturally occurring fibers bundled with pectin to substantially remove pectin and form substantially individualized fibers;
carding the substantially individualized fibers to form a randomly arrayed fiber web;
bonding the randomly arrayed fiber web to form the nonwoven fabric having a support surface;
disposing the adhesive onto either the support surface of the nonwoven fabric or a surface of the film;
disposing the film onto the support surface of the nonwoven fabric; and
nipping to form the laminate.

75. The method of claim 74, wherein the film comprises a polyethylene polymer, a polyethylene copolymer, a polypropylene polymer, a polypropylene copolymer, a polyurethane polymer, a polyurethane copolymer, or a styrenebutadiene copolymer.

76. The method of claim 74, wherein the film comprises linear low density polyethylene.

77. The method of claim 74, wherein the adhesive is a sprayable latex, a polyalphaolefin, or an ethylene vinyl acetate.

78. A laminate comprising a first nonwoven fabric and another fabric bonded to the first nonwoven fabric, the first nonwoven fabric being the nonwoven fabric of claim 58, the another fabric being at least one of a second nonwoven fabric or a woven fabric, the second nonwoven fabric optionally being an additional nonwoven fabric of claim 58.

79. The laminate of claim 78, wherein the another fabric is bonded to the first nonwoven fabric with an adhesive.

80. A nonwoven fabric formed of a majority of fibers comprising substantially straight, full length natural individualized bast fibers with less than 10% of the pectin content of the naturally occurring bundled bast fiber from which the individualized bast fibers are derived, the individualized bast fibers being formed into an unbounded web in the dry state, and the bast fibers being smooth and elongated and having a mean length greater than 12 mm.

81. The nonwoven fabric of claim 80, wherein the web is formed by a method employing a mechanical card.

82. The nonwoven fabric of claim 80, wherein the web is formed by a method employing a combination of a mechanical card and a forced air stream.

83. The nonwoven fabric of claim 80, wherein the web is bonded by hydroentangling.

84. The nonwoven fabric of claim 80, wherein the hydroentangled web is treated with an aqueous adhesive and exposed to heat.

85. The nonwoven fabric of claim 80, wherein the web is bonded by mechanical needle punching.

86. The nonwoven fabric of claim 80, wherein the web is bonded by passing a heated air stream through the web.

87. The nonwoven fabric of claim 80, wherein the web is bonded by applying an aqueous adhesive to the unbounded web and exposing the web to heat.

88. The nonwoven fabric of claim 80, wherein the individualized bast fibers comprise less than 20% by weight of the pectin content of the naturally occurring bundled bast fiber.

89. The nonwoven fabric of claim 80, wherein the individualized bast fibers comprise less than 0.15% by weight of the pectin content of the naturally occurring bundled bast fiber.

90. A method of making the nonwoven fabric of claim 80, the method comprising:
    chemically treating naturally occurring fibers to substantially remove pectin and form substantially individualized fibers;
    carding the substantially individualized fibers to form a randomly arrayed fiber web; and
    bonding the randomly arrayed fiber web to form the nonwoven fabric.

91. The method of claim 90, further comprising adding thermoplastic fibers to the substantially individualized fibers and thermal bonding the nonwoven fabric.

92. The method of claim 90, wherein bonding is hydroentangling.

93. The method of claim 90, wherein bonding is mechanical needle punching.

94. The method of claim 90, wherein bonding is passing a heated air stream through the web.

95. A laminate comprising the nonwoven fabric of claim 80, a film, and an adhesive disposed between the fabric and the film.

96. The laminate of claim 95, wherein the film comprises a polyethylene polymer, a polyethylene copolymer, a polypropylene polymer, a polypropylene copolymer, a polyurethane polymer, a polyurethane copolymer, or a styrenebutadiene copolymer.

97. The laminate of claim 95, wherein the film comprises linear low density polyethylene.

98. The laminate of claim 95, wherein the adhesive is a sprayable latex, a polyalphaolefin, or an ethylene vinyl acetate.

99. The laminate of claim 95, wherein the film is a breathable film.

100. A method of making the laminate of claim 95, the method comprising:
    chemically treating naturally occurring fibers bundled with pectin to substantially remove pectin and form substantially individualized fibers;
    carding the substantially individualized fibers to form a randomly arrayed fiber web;
    bonding the randomly arrayed fiber web to form the nonwoven fabric having a support surface;
    disposing the adhesive onto either the support surface of the nonwoven fabric or a surface of the film;
    disposing the film onto the support surface of the nonwoven fabric; and
    nipping to form the laminate.

101. The method of claim 100, wherein the film comprises a polyethylene polymer, a polyethylene copolymer, a polypropylene polymer, a polypropylene copolymer, a polyurethane polymer, a polyurethane copolymer, or a styrenebutadiene copolymer.

102. The method of claim 100, wherein the film comprises linear low density polyethylene.

103. The method of claim 100, wherein the adhesive is a sprayable latex, a polyalphaolefin, or an ethylene vinyl acetate.

104. A laminate comprising a first nonwoven fabric and another fabric bonded to the first nonwoven fabric, the first nonwoven fabric being the nonwoven fabric of claim 80, the another fabric being at least one of a second nonwoven fabric or a woven fabric, the second nonwoven fabric optionally being an additional nonwoven fabric of claim 80.

105. The laminate of claim 104, wherein the another fabric is bonded to the first nonwoven fabric with an adhesive.

106. A nonwoven fabric comprising about 85 weight percent individualized fibers and about 15 weight percent regenerated cellulose fibers, based upon total fiber weight, the fibers being full length natural individualized fibers which are substantially straight, plant-based, smooth and elongated, and substantially pectin-free and have a mean length greater than 6 mm.

107. The nonwoven fabric of claim 106, wherein the substantially straight, plant-based, smooth and elongated, substantially pectin-free fibers are bast fibers.

108. The nonwoven fabric of claim 106, wherein the substantially straight, plant-based, smooth and elongated, substantially pectin-free fibers are fibers extracted from flax, hemp, jute, ramie, nettle, Spanish broom, kenaf plants, or any combination thereof.

109. The nonwoven fabric of claim 106, wherein the substantially straight, plant-based, smooth and elongated, substantially pectin-free fibers have less than 10% by weight of the pectin content of the naturally occurring fibers from which the substantially pectin-free fibers are derived.

110. The nonwoven fabric of claim 106, wherein the substantially straight, plant-based, smooth and elongated, substantially pectin-free fibers have less than 15% by weight of the pectin content of the naturally occurring fibers from which the substantially pectin-free fibers are derived.

111. The nonwoven fabric of claim 106, wherein the substantially straight, plant-based, smooth and elongated, substantially pectin-free fibers have less than 20% by weight of the pectin content of the naturally occurring fibers from which the substantially pectin-free fibers are derived.

112. The nonwoven fabric of claim 106, wherein the substantially straight, plant-based, smooth and elongated, substantially pectin-free fibers having a mean length of at least 7 mm.

113. The nonwoven fabric of claim 106, wherein the substantially straight, plant-based, smooth and elongated, substantially pectin-free fibers have a mean length of at least 8 mm.

114. The nonwoven fabric of claim 106, wherein the substantially straight, plant-based, smooth and elongated, substantially pectin-free fibers having a mean length of at least 9 mm.

115. The nonwoven fabric of claim 106, wherein the substantially straight, plant-based, smooth and elongated, substantially pectin-free fibers have a mean length of at least 10 mm.

116. The nonwoven fabric of claim 106, wherein the substantially straight, plant-based, smooth and elongated, substantially pectin-free fibers have a mean length greater than 12 mm.

117. The nonwoven fabric of claim 106, wherein the nonwoven fabric is a wet wiper, a dry wiper, an impregnated wiper, a sorbent, a medical supply product, a personal protective fabric, an automotive protective covering, a personal care article, a fluid filtration product, a home furnishing product, a thermal insulation product, an acoustic insulation product, an agricultural application product, a landscaping application product, or a geotextile application product.

118. The nonwoven fabric of claim 106, wherein the nonwoven fabric is a baby wipe, a cosmetic wipe, a perinea wipe, a disposable washcloth, a kitchen wipe, a bath wipe, a hard surface wipe, a glass wipe, a mirror wipe, a leather wipe, an electronics wipe, a lens wipe, a polishing wipe, a medical cleaning wipe, a disinfecting wipe, a surgical drape, a surgical gown, a wound care product, a protective coverall, a sleeve protector, a diaper, a feminine care article, a nursing pad, an air filter, a water filter, an oil filter, or a furniture backing.

119. The nonwoven fabric of claim 106, wherein the nonwoven fabric has thermoplastic fibers substantially dispersed among the individualized fibers and the nonwoven fabric has a pattern present on at least one surface.

120. A method of making the nonwoven fabric of claim 106, the method comprising:
chemically treating naturally occurring fibers to substantially remove pectin and form substantially individualized fibers;
carding the substantially individualized fibers to form a randomly arrayed fiber web; and
bonding the randomly arrayed fiber web to form the nonwoven fabric.

121. The method of claim 120, further comprising adding thermoplastic fibers to the individualized fibers and thermal bonding the nonwoven fabric.

122. The method of claim 120, wherein bonding is hydroentangling.

123. The method of claim 120, wherein bonding is mechanical needle punching.

124. The method of claim 120, wherein bonding is passing a heated air stream through the web.

125. A laminate comprising the nonwoven fabric of claim 106, a film, and an adhesive disposed between the fabric and the film.

126. The laminate of claim 125, wherein the film comprises a polyethylene polymer, a polyethylene copolymer, a polypropylene polymer, a polypropylene copolymer, a polyurethane polymer, a polyurethane copolymer, or a styrenebutadiene copolymer.

127. The laminate of claim 125, wherein the film comprises linear low density polyethylene.

128. The laminate of claim 125, wherein the adhesive is a sprayable latex, a polyalphaolefin, or an ethylene vinyl acetate.

129. The laminate of claim 125, wherein the film is a breathable film.

130. A method of making the laminate of claim 125, the method comprising:
chemically treating naturally occurring fibers bundled with pectin to substantially remove pectin and form substantially individualized fibers;
carding the substantially individualized fibers to form a randomly arrayed fiber web;
bonding the randomly arrayed fiber web to form the nonwoven fabric having a support surface;
disposing the adhesive onto either the support surface of the nonwoven fabric or a surface of the film;
disposing the film onto the support surface of the nonwoven fabric; and
nipping to form the laminate.

131. The method of claim 130, wherein the film comprises a polyethylene polymer, a polyethylene copolymer, a polypropylene polymer, a polypropylene copolymer, a polyurethane polymer, a polyurethane copolymer, or a styrenebutadiene copolymer.

132. The method of claim 130, wherein the film comprises linear low density polyethylene.

133. The method of claim 130, wherein the adhesive is a sprayable latex, a polyalphaolefin, or an ethylene vinyl acetate.

134. A laminate comprising a first nonwoven fabric and another fabric bonded to the first nonwoven fabric, the first nonwoven fabric being the nonwoven fabric of claim 106, the another fabric being at least one of a second nonwoven fabric or a woven fabric, the second nonwoven fabric optionally being an additional nonwoven fabric of claim 106.

135. The laminate of claim 134, wherein the another fabric is bonded to the first nonwoven fabric with an adhesive.

* * * * *